(12) United States Patent
Lisi et al.

(10) Patent No.: US 11,382,556 B2
(45) Date of Patent: Jul. 12, 2022

(54) BRAIN ACTIVITY ANALYZING APPARATUS, BRAIN ACTIVITY ANALYZING METHOD, PROGRAM AND BIOMARKER APPARATUS

(71) Applicant: ADVANCED TELECOMMUNICATIONS RESEARCH INSTITUTE INTERNATIONAL, Kyoto (JP)

(72) Inventors: Giuseppe Lisi, Soraku-gun (JP); Jun Morimoto, Soraku-gun (JP); Mitsuo Kawato, Soraku-gun (JP); Noriaki Yahata, Soraku-gun (JP)

(73) Assignee: ADVANCED TELECOMMUNICATIONS RESEARCH INSTITUTE INTERNATIONAL, Soraku-gun (JP)

( * ) Notice: Subject to any disclaimer, the term of this patent is extended or adjusted under 35 U.S.C. 154(b) by 1009 days.

(21) Appl. No.: 15/779,011

(22) PCT Filed: Nov. 22, 2016

(86) PCT No.: PCT/JP2016/084567
§ 371 (c)(1),
(2) Date: May 24, 2018

(87) PCT Pub. No.: WO2017/090590
PCT Pub. Date: Jun. 1, 2017

(65) Prior Publication Data
US 2020/0163609 A1 May 28, 2020

(30) Foreign Application Priority Data
Nov. 24, 2015 (JP) .............................. JP2015-228970

(51) Int. Cl.
*A61B 5/00* (2006.01)
*G01R 33/48* (2006.01)
*G06T 7/00* (2017.01)

(52) U.S. Cl.
CPC ........ *A61B 5/4064* (2013.01); *G01R 33/4806* (2013.01); *G06T 7/0012* (2013.01);
(Continued)

(58) Field of Classification Search
CPC ................ A61B 5/4064; A61B 5/7246; A61B 2576/026; A61B 5/055; G01R 33/4806;
(Continued)

(56) References Cited

U.S. PATENT DOCUMENTS

2015/0248615 A1 9/2015 Parra et al.
2015/0272461 A1 10/2015 Morimoto et al.
2015/0294074 A1 10/2015 Kawato et al.

FOREIGN PATENT DOCUMENTS

JP 2011-000184 A 1/2011
JP 2013-218725 A 10/2013
(Continued)

OTHER PUBLICATIONS

Decharms et al., "Control over brain activation and pain learned by using real-time functional MRI", Proceedings of the National Academy of Sciences of the United States of America, vol. 102, No. 51, Dec. 20, 2005, pp. 18626-18631.
(Continued)

*Primary Examiner* — Alazar Tilahun
(74) *Attorney, Agent, or Firm* — Birch, Stewart, Kolasch & Birch, LLP

(57) ABSTRACT

[Object] An object is to provide a brain activity analyzing method for realizing a biomarker using brain function imaging for neurological/mental disorders.
[Solution] From data of resting-state functional connectivity MRI obtained by measuring groups of healthy subjects and patients, a correlation matrix of degrees of activities among prescribed brain regions is derived. By a sparse canonical correlation analysis (SCCA) of attributes of subjects and the correlation matrix, elements of correlation matrix that connect to canonical variables corresponding only to the diagnosis label are extracted. By sparse logistic regression (SLR) during Leave-One-Out Cross Validation of a first sum-set of elements of correlation matrix obtained as a result of feature
(Continued)

extraction by a sparse regularized canonical correlation analysis, a second sum-set of elements of the correlation matrix is extracted. By discrimination analysis using sparse logistic regression on the second sum-set, a discriminator is generated.

17 Claims, 22 Drawing Sheets

(52) U.S. Cl.
CPC .............. *G06T 2207/10088* (2013.01); *G06T 2207/30016* (2013.01)

(58) Field of Classification Search
CPC ......... G06T 7/0012; G06T 2207/10088; G06T 2207/30016; G06T 7/0014; G16H 30/40
See application file for complete search history.

(56) References Cited

FOREIGN PATENT DOCUMENTS

| JP | 2014-084567 | A | 5/2014 |
|---|---|---|---|
| JP | 2015-062817 | A | 4/2015 |
| WO | WO 2006/132313 | A1 | 12/2006 |
| WO | WO 2019/069955 | A1 | 4/2019 |

OTHER PUBLICATIONS

Kamitani et al., "Decoding the visual and subjective contents of the human brain", Nature Neuroscience, 2005; vol. 8, No. 5, May 2005, pp. 679-685.
Li et al., "Group Study of Simulated Driving fMRI Data by Multiset Canonical Correlation Analysis", Journal of Signal Processing Systems, vol. 68, 2012, pp. 31-48.
Oldfield, "The Assessment and Analysis of Handedness: The Edinburgh Inventory", Neuropsychologia, vol. 9, 1971, pp. 97-113.
Perrot et al., "Cortical sulci recognition and spatial normalization", Medical Image Analysis, vol. 15, 2011, pp. 529-550.
Raichle et al., "A default mode of brain function", Proceedings of the National Academy of Sciences of the United States of America, vol. 98, No. 2, Jan. 16, 2001, pp. 676-682.
Schonfelder et al., "Sparse regularized regression identifies behaviorally-relevant stimulus features from psychophysical data", The Journal of the Acoustical Society of America, vol. 131, No. 5, May 2012, pp. 3953-3969.
Tzourio-Mazoyer et al., "Automated Anatomical Labeling of Activations in SPM Using a Macroscopic Anatomical Parcellation of the MNI MRI Single-Subject Brain", NeuroImage, vol. 15, 2002, pp. 273-289.
Weiskopf, "Real-time fMRI and its application to neurofeedback", NeuroImage, vol. 62, 2012, pp. 682-692.
Witten et al., "A penalized matrix decomposition, with applications to sparse principal components and canonical correlation analysis", Biostatistics, vol. 10, No. 3, 2009, pp. 515-534.
Yamashita et al., "Sparse estimation automatically selects voxels relevant for the decoding of fMRI activity patterns", NeuroImage, vol. 42, No. 4, Oct. 1, 2008, pp. 1414-1429.

OFF-DIAGONAL LOWER TRIANGLE
OF CORRELATION MATRIX

Fig. 19

|  | SITE A | | SITE B | | SITE C | |
|---|---|---|---|---|---|---|
|  | ASD | TD | ASD | TD | ASD | TD |
| MALE/FEMALE | 23/12 | 20/18 | 35/4 | 30/6 |  | 23/10 |
| AGE | 31.9 ± 8.8 | 36.6 ± 8.3 | 31.0 ± 8.2 | 30.9 ± 6.9 |  | 24.2 ± 5.3 |
| DOMINANT HAND | 91.9 ± 13.2 | 92.8 ± 15.3 | 87.9 ± 27.7 | 95.1 ± 18.3 | RIGHT-HANDED | |
| IQ | 104.7 ± 13.1 | 107.9 ± 7.4 | 110.4 ± 8.6 | 109.5 ± 8.3 | NR | |

NR, NO RECORD

Fig. 21

| SITE ID | ASD | | | TD | | |
|---|---|---|---|---|---|---|
| | AGE | SEX (MALE/FEMALE) | FIQ | AGE | SEX (MALE/FEMALE) | FIQ |
| CAL | 23.9 ± 6.2 | 5/2 | 103.0 ± 10.6 | 26.5 ± 8.3 | 4/2 | 114.7 ± 10.8 |
| CMA | 21.5 ± 0.7 | 2/0 | 117.5 ± 13.4 | 22.3 ± 2.3 | 3/0 | 106.7 ± 4.9 |
| NYU | 19.6 | 1/0 | 94.0 | 19.1 | 1/0 | 107.0 |
| OLN | 19.0 ± 1.4 | 2/0 | 109.0 ± 12.7 | 20.5 ± 0.7 | 2/0 | 116.5 ± 20.5 |
| PIT | 23.2 ± 4.4 | 6/0 | 118.2 ± 16.5 | 22.6 ± 3.3 | 6/0 | 113.5 ± 11.4 |
| TTY | 20.8 ± 2.6 | 8/0 | 114.5 ± 11.2 | 21.2 ± 2.6 | 8/0 | 115.1 ± 10.2 |
| USM | 26.9 ± 8.3 | 18/0 | 108.1 ± 14.0 | 25.8 ± 4.9 | 18/0 | 113.2 ± 14.3 |
| TOTAL | 24.0 ± 6.6 | 42/2 | 110.0 ± 13.6 | 24.0 ± 5.0 | 42/2 | 113.3 ± 12.0 |

BRAIN ACTIVITY ANALYZING APPARATUS, BRAIN ACTIVITY ANALYZING METHOD, PROGRAM AND BIOMARKER APPARATUS

TECHNICAL FIELD

The present invention relates to a brain activity analyzing apparatus, a brain activity analyzing method and a biomarker apparatus, utilizing functional brain imaging.

BACKGROUND ART (Biomarker)

When biological information is converted into a numerical value and quantified as an index for quantitatively comprehending biological changes in a living body, it is called a "biomarker."

According to FDA (United States Food and Drug Administration), a biomarker is regarded as "a characteristic that is objectively measured and evaluated as an indicator of normal biological processes, pathogenic processes or pharmacological responses to a therapeutic intervention." Biomarkers representative of a state of or a change in a disease, or a degree of healing are used as surrogate markers (substitute markers) to monitor efficacy in clinical tests of new drugs. The blood sugar level, the cholesterol level and the like, are representative biomarkers used as indexes of lifestyle diseases. Biomarkers include not only substances of biological origin contained in urine or blood but also electrocardiogram, blood pressure, PET images, bone density, lung function and the like. Developments in genomic analysis and proteome analysis have lead to discovery of various biomarkers related to DNA, RNA or biological protein.

Biomarkers are promising for measuring therapeutic efficacy after the onset of a disease and, in addition, as routine preventive indexes, promising for disease prevention. Further, application of biomarkers to individualized medicine for selecting effective treatment avoiding side effects is expected.

In the field of neurological/mental disorders, however, though molecular markers and the like usable as objective indexes from a biochemical or molecular genetics viewpoint have been studied, it should in fairness be stated that they are still in a research phase.

Meanwhile, a disease determination system has been reported which uses an NIRS (Near-InfraRed Spectroscopy) technique to classify mental disorders such as schizophrenia and depression based on features of hemoglobin signals measured by biological optical measurement (First Patent Literature).

(Real Time Neurofeedback)

Conventionally, as the therapy for Obsessive-Compulsive Disorder (OCD) as one type of neurotic disease, for example, pharmacological and behavioral treatments have been known. The pharmacological treatment uses, for example, a serotonin-selective reuptake inhibitor. As the behavioral treatment, exposure response prevention therapy, combining exposure therapy and response prevention has been known.

Meanwhile, real time neurofeedback is studied as the possible therapy for a neurological/mental disorder.

Functional brain imaging, such as functional Magnetic Resonance Imaging (fMRI), which visualizes hemodynamic reaction related to human brain activities using Magnetic Resonance Imaging (MRI), has been used to specify an active region of a brain corresponding to a component of a brain function of interest, that is, to clarify cerebral localization of function, by detecting differences between those in brain activities while responding to a sensory stimulus or performing a cognitive task, and those brain activities in a resting state or while performing a control task.

Recently, the real time neurofeedback technique using functional brain imaging such as functional magnetic response imaging (fMRI) is reported (First Non-Patent Literature). The real time neurofeedback technique is now attracting attention as possible therapy for neurological disorders and mental disorders.

Neurofeedback is one type of bio-feedback, in which a subject receives feedback about his/her brain activities in order to learn how to manage his/her brain activities.

By way of example, according to a report, when measurements of activities of anterior cingulate gyrus were fed back to patients on a real time basis as larger or smaller fire images, and the patients were instructed to make efforts to decrease the size of the fire, then improvement was attained both in real-time and long-term chronic pain of central origin (see Second Non-Patent Literature).

(Resting State fMRI)

Further, recent studies show that even when a subject is in the resting state, his/her brain works actively. Specifically, in the brain, there is a group of nerve cells that subside when the brain works actively and are excited vigorously when the brain is in the resting state. Anatomically, these cells mainly exist on the medial surfaces where left and right cerebral hemispheres are connected, namely, the medial surface of the frontal lobe, the posterior cingulate cortex, the precuneus, the posterior portion of the parietal association area and the middle temporal gyrus. These regions representing baseline brain activities in the resting state are named Default Mode Network (DMN) and these regions work in synchronization as one network (see Third Non-Patent Literature).

An example of a difference in brain activities between those of a healthy individual and those of a patient with a mental disease is observed in brain activities in the default mode network. The default mode network refers to portions of one's brain that exhibit more positive brain activities when a subject is in the resting state than when the subject is performing a goal-oriented task. It has been reported that abnormality has been observed in the default mode networks of patients with mental disorders such as schizophrenia or Alzheimer's disease as compared with healthy individuals. By way of example, it is reported that in the brain of a schizophrenia patient, correlation of activities among the posterior cingulate cortex, which belongs to the default mode network, and parietal lateral cortex, medial prefrontal cortex or cerebellar cortex, is decreased in the resting state.

However, it is not necessarily clear how the default mode network relates to the cognitive function, or how the correlations of functional connections among brain regions relates to the above-described neurofeedback.

On the other hand, observed changes in correlations between activities among a plurality of brain regions caused, for example, by a difference in tasks are used to evaluate functional connections among these brain regions. Specifically, the evaluation of functional connections in the resting state obtained by fMRI is called resting-state functional connection MRI (rs-fcMRI), which is utilized for clinical studies directed to various neurological/mental disorders. The conventional rs-fcMRI, however, is for observing activities of a global neural network such as the default mode network described above, and more detailed functional connections are yet to be sufficiently considered.

(Nuclear Magnetic Resonance Imaging)

Nuclear Magnetic Resonance Imaging will be briefly described in the following.

Conventionally, as a method of imaging cross-sections of the brain or the whole body of a living body, nuclear magnetic resonance imaging has been used, for example, for human clinical diagnostic imaging, which method utilizes nuclear magnetic resonance with atoms in the living body, particularly with atomic nuclei of hydrogen atoms.

As compared with "X-ray CT," which is a similar method of human tomographic imaging, characteristics of nuclear magnetic resonance imaging when applied to a human body, for example, are as follows:

(1) An image with the density distribution is obtained reflecting the distribution of hydrogen atoms and their signal relaxation time (reflecting strength of atomic bonding). Therefore, the shadings present different natures of tissues, making it easier to observe a difference in tissues;

(2) The magnetic field is not absorbed by bones. Therefore, a portion surrounded by a bone or bones (for example, inside one's skull, or spinal cord) can easily be observed; and (3) Unlike X-rays, it is not harmful to human body and, hence, it has a wide range of possible applications.

Nuclear magnetic resonance imaging described above uses the magnetic property of hydrogen atomic nuclei (protons), which are most abundant in human cells and have highest magnetism. Motion in a magnetic field of spin angular momentum associated with the magnetism of hydrogen atomic nucleus is, classically, compared to the precession of a spinning top.

In the following, as a description of the background of the present invention, the principle of magnetic resonance will be summarized using the intuitive classical model.

The direction of spin angular momentum of a hydrogen atomic nucleus (the direction of the axis of the rotation of a spinning top) is random in an environment free of magnetic field. When a static magnetic field is applied, however, the momentum is aligned with the line of magnetic force.

In this state, when an oscillating magnetic field is superposed and the frequency of the oscillating magnetic field is the resonance frequency $f0=\gamma B0/2\pi$ ($\gamma$: substance-specific coefficient) determined by the intensity of the static magnetic field, energy moves to the side of atomic nuclei because of resonance, and the direction of magnetic vector changes (precession increases). When the oscillating magnetic field is turned off in this state, the precession gradually returns to the direction in the static magnetic field with the tilt angle returning to the previous angle. By externally detecting this process by an antenna coil, an NMR signal can be obtained. "NMR" stands for Nuclear Magnetic Resonance.

The resonance frequency $f0$ mentioned above of hydrogen atom is $42.6 \times B0$ (MHz) where B0 (T) represents the intensity of the static magnetic field.

Further, in nuclear magnetic resonance imaging, changes appearing in detected signals in accordance with changes in the blood stream makes it possible to visualize an active portion of a brain activated in response to an external stimulus. Such a nuclear magnetic resonance imaging is specifically referred to as fMRI (functional MRI).

An fMRI uses a common MRI apparatus with additional hardware and software necessary for fMRI measurement.

The changes in blood stream cause changes in NMR signal intensity, since oxygenated hemoglobin and deoxygenated hemoglobin in the blood have magnetic properties different from each other. Hemoglobin is diamagnetic when oxygenated, and it does not have any influence on relaxation time of hydrogen atoms in the surrounding water. In contrast, hemoglobin is paramagnetic when deoxygenated, and it changes surrounding magnetic field. Therefore, when the brain receives any stimulus and local blood stream increases and oxygenated hemoglobin increases, the change can be detected by the MRI signals. The stimulus to a subject may include visual stimulus, audio stimulus, or performance of a prescribed task (see, for example, Second Patent Literature).

Note that, in the studies of the brain functions, brain activities are measured by measuring increase in the nuclear magnetic resonance signal (MRI signal) of hydrogen atoms corresponding to a phenomenon where the density of deoxygenated hemoglobin in red blood cells decrease in minute veins or capillary vessels (BOLD effect).

Particularly, in studies related to the human motor functions, brain activities are measured by the MRI apparatus as described above while a subject or subjects are performing some physical activity.

For human subjects, it is necessary to measure the brain functions in a non-invasive manner. In this aspect, a decoding technique enabling, extraction of more detailed information from fMRI data has been developed (see, for example, Fourth Non-Patent Literature). Specifically, a voxel-by-voxel brain activity analysis (volumetric pixel: voxel) of the brain by the fMRI enables the estimation of stimulus input and the state of recognition from spatial patterns of the brain activities.

Further, as a development of such a decoding technique. Third Patent Literature discloses a method of brain function analysis for realizing, biomarkers based on functional brain imaging for a neurological/mental disorder. According to this method, from measurement data of resting-state functional connection MRI of healthy individuals and patients, a correlation matrix of degrees of activities between prescribed brain regions is derived for each subject. Feature extraction is performed by regularized canonical correlation analysis on the correlation matrix and on the attributes of subjects including disease/healthy labels of the subjects. Based on the results of regularized canonical correlation analysis, a discriminator that functions as a biomarker is generated from discriminant analysis by sparse logistic regression (SLR). It has been indicated that by such a technique of machine learning, results of mental disease diagnosis can be predicted based on connections among brain regions derived from fMRI data in the resting state. Further, verification of the prediction performance indicated that prediction is not only applicable to the brain activities measured in a certain facility but also generalizable, to some extent, to the brain activities measured in a different facility.

CITATION LIST

Patent Literature

First PTL: National Publication No. 2006-132313

Second PTL: Japanese Patent Laying-Open No. 2011-000184

Third PTL: Japanese Patent Laying-Open No. 2015-062817

Non Patent Literature

First NPL: Nikolaus Weiskopf, "Real-time fMRI and its application to neurofeedback", NeuroImage 62 (2012) 682-692

Second NPL: deCharms R C, Maeda F, Glover G H et al, "Control over brain activation and pain learned by using real-time functional MRI", Proc Natl Acad Sci USA 102 (51), 18626-18631, 2005

Third NPL: Raichle M E, Macleod A M, Snyder A Z, et al. "A default mode of brain function", Proc Natl Acad Sci USA 98(2), 676-682, 2001

Fourth NPL: Kamitani Y, Tong F. Decoding the visual and subjective contents of the human brain. Nat Neurosci. 2005; 8: 679-85.

SUMMARY OF INVENTION

Technical Problem

When we consider application to treatment of a neurological/mental disorder of the brain activity analysis by functional brain imaging such as functional Magnetic Resonance Imaging as described above, the analysis of brain activities using functional brain imaging as the above-described biomarker is promising as a non-invasive functional marker, and applications to development of diagnostic method and to searching/identification of target molecules aiming toward drug discovery for realizing basic remedy are also expected.

By way of example, consider a mental disorder such as autism. Practical biomarker using genes is not yet established and, therefore, development of therapeutic agents remains difficult, since it is difficult to determine effect of medication.

In order to generate a discriminator by machine learning based on measured data of brain activities and to practically use this as a biomarker, it is necessary to improve prediction accuracy of the biomarker generated by machine learning for the brain activities measured at one facility. Further, it is necessary that the biomarker generated in this manner can be generalized to brain activities measured at other facilities.

Specifically, when a discriminator is to be built by machine learning based on measured data of brain activities, the following two main problems must be addressed.

The first problem is the small size of samples.

The amount of data N representing the number of subjects is far smaller than the dimension M of measured data of brain activities, parameters of the discriminator will easily be over-fitted to the training data.

Because of this over-fitting, the discriminator thus built exhibits very poor performance on newly sampled test data. The reason for this is that the test data were not used for training the discriminator.

Therefore, in order to discriminate and use essential features only with respect to desired generalization of the discriminator, appropriate regularization must be introduced.

The second problem is that the discriminator is clinically effective and scientifically reliable only when the built discriminator maintains satisfactory performance on MRI data scanned at an imaging site different form the site where the training data were collected.

This is a so-called generalization capability over a plurality of imaging sites.

In clinical applications, however, it is often observed that a discriminator trained by using data obtained at a specific site cannot be generalized to data scanned at a different site.

The present invention was made to solve the above-described problems and its object is to provide a brain activity analyzing apparatus and a brain activity analyzing method that are capable of providing data which establishes a basis for objective determination as to whether the brain activity is in a healthy/disease state.

Another object of the present invention is to provide a brain activity analyzing apparatus and a brain activity analyzing method for realizing a method of determination using brain function imaging for supporting the diagnosis of neurological/mental disorders.

A further object of the present invention is to provide a brain activity analyzing apparatus, a brain activity analyzing method and a biomarker apparatus for realizing a biomarker utilizing brain function imaging.

Solution to Problem

According to one aspect, the present invention provides a brain activity analyzing apparatus, including a discriminator generating means for generating a discriminator from signals obtained by a brain activity detecting means for time-sequentially measuring in advance signals representing brain activities at a plurality of prescribed regions in a brain of each of a plurality of subjects; wherein a plurality of attribute information items are associated to each of the plurality of subjects; the discriminator generating means includes: i) a correlation matrix calculating means for calculating, for each of the subjects, a correlation matrix of brain activities among the plurality of prescribed regions from the measured signals; ii) a first feature extracting means for extracting elements of the correlation matrix that connect to a canonical variable corresponding only to a specific attribute information item among the plurality of attribute information items by successively selecting, from M (M: natural number not smaller than 2) different subsets extracted from the plurality of subjects, one subset and by performing sparse canonical correlation analysis on the attribute information items and on elements of the correlation matrix of (M-1) subsets except for the selected one subset; iii) a first sum-set extracting means for obtaining, for the successively selected subsets, a first sum-set as a sum-set of elements of the extracted correlation matrix; and iv) a discriminator calculating means for generating a discriminator for estimating the specific attribute information item from the elements of the first sum-set; the brain activity analyzing apparatus further including: a storage means for storing an information item for specifying the calculated discriminator; and a discriminating means for performing a process of discriminating input data based on the discriminator specified by the information item stored in the storage means.

Preferably, the discriminator calculating means calculates the discriminator for estimating the specific attribute information item from the first sum-set by sparse logistic regression.

Preferably, the discriminator generating means further includes, when subjects other than the above-described M subsets of the plurality of subjects are used as a test set and the test set is divided into N (N: natural number not smaller than 2) different groups, a second feature extracting means for calculating, by sparse logistic regression a test discriminator for estimating the specific attribute information item based on the first sum-set, on a set of subjects except for one group selected from the N groups of the plurality of subjects, and for extracting, along with sparsing, elements of the correlation matrix as the explanatory variables of the test discriminator, and a second sum-set extracting means for iterating feature extraction by the second feature extracting means while successively selecting one group from the N groups for obtaining a second sum-set as the sum-set of elements of the correlation matrix extracted as the explanatory variables of the test discriminator; and the discriminator calculating means calculates the discriminator for estimating the specific attribute information item from the second sum-set by sparse logistic regression.

Preferably, the discriminator generating means further includes a cross-validation means for performing cross-validation by calculating a result of discrimination by the test discriminator calculated by the second feature extracting means while successively selecting one group to be excluded from the N groups, using the excluded group as a test sample.

Preferably, the specific attribute information item is a diagnosis label of a subject.

According to another aspect, the present invention provides a program causing a computer having a processing device and a storage device to execute brain activity analysis based on information from a brain activity detecting device for measuring brain activities of a plurality of subjects; wherein a plurality of attribute information items are associated to each of the plurality of subjects; the program causes the computer to execute a step of the processing device generating a discriminator, from information obtained by the brain activity detecting device time-sequentially measuring in advance brain activities at a plurality of prescribed regions in a brain of each of a plurality of subjects; the step of generating a discriminator includes the steps of: i) calculating, for each of the subjects, a correlation matrix of brain activities among the plurality of prescribed regions from the measured signals; ii) extracting elements of the correlation matrix that connect to a canonical variable corresponding only to a specific attribute information item among the plurality of attribute information items by successively selecting, from M (M: natural number not smaller than 2) different subsets extracted from the plurality of subjects, one subset and by performing sparse canonical correlation analysis on the attribute information items and on elements of the correlation matrix of (M-1) subsets except for the selected one subset; iii) obtaining, for the successively selected subsets, a first sum-set as a sum-set of elements of the extracted correlation matrix; and iv) calculating a discriminator for estimating the specific attribute information item from the elements of the first sum-set; the program further causes the computer to execute the steps of: storing an information item for specifying the calculated discriminator in the storage device; and performing a process of discriminating input data based on the discriminator specified by the information item stored in the storage device.

Preferably, the step of calculating a discriminator includes the step of calculating the discriminator for estimating the specific attribute information item from the first sum-set by sparse logistic regression.

Preferably, the step of generating a discriminator includes the steps of: when subjects other than the above-described M subsets of the plurality of subjects are used as a test set and the test set is divided into N (N: natural number not smaller than 2) different groups, calculating, by sparse logistic regression a test discriminator for estimating the specific attribute information item based on the first sum-set, on a set of subjects except for one group selected from the N groups of the plurality of subjects, and extracting, along with sparsing, elements of the correlation matrix as the explanatory variables of the test discriminator; and iterating feature extraction at the step of extracting elements while successively selecting one group from N groups and thereby obtaining a second sum-set as the sum-set of elements of the correlation matrix extracted as the explanatory variables the of test discriminator; and at the step of calculating a discriminator, the discriminator for estimating the specific attribute information item from the second sum-set is calculated by sparse logistic regression.

Preferably, the step of generating a discriminator further includes the step of performing cross-validation by calculating a result of discrimination by the test discriminator calculated at the step of extracting elements while successively selecting one group to be excluded from the N groups, using the excluded group as a test sample.

Preferably, the specific attribute information item is a diagnosis label of a subject.

According to a still further aspect, the present invention provides a brain activity analyzing apparatus, including a discriminator generating device for generating a discriminator from signals obtained by a brain activity detecting device time-sequentially measuring in advance signals representing brain activities at a plurality of prescribed regions in a brain of each of a plurality of subjects. A plurality of attribute information items are associated to each of the plurality of subjects. The discriminator is for estimating a specific attribute information item of a subject. The brain activity analyzing apparatus further includes: a storage device connected to the discriminator generating device for storing information for specifying a discriminator generated by the discriminator generating device; and a discriminating device for performing a process of discriminating input data based on the discriminator specified by the information item stored in the storage device. The discriminator generating device includes a processor. The processor is programmed to: i) calculate, for each of the subjects, a correlation matrix of brain activities among the plurality of prescribed regions from the measured signals; ii) extract elements of the correlation matrix that connect to a canonical variable corresponding only to a specific attribute information item among the plurality of attribute information items by successively selecting, from M (M: natural number not smaller than 2) different subsets extracted from the plurality of subjects, one subset and by performing a sparse canonical correlation analysis on the attribute information items and on elements of the correlation matrix of (M-1) subsets except for the selected one subset; iii) obtain, for the successively selected subsets, a first sum-set as a sum-set of elements of the extracted correlation matrix; and iv) calculate a discriminator for estimating the specific attribute information item from the elements of the first sum-set.

According to a still further aspect, the present invention provides a brain activity analyzing method causing a computer having a processing device and a storage device to execute brain activity analysis based on information from a brain activity detecting device for measuring brain activities of a plurality of subjects; wherein a plurality of attribute information items are associated to each of the plurality of subjects; the method including a step of the processing device generating a discriminator, from information obtained by the brain activity detecting device time-sequentially measuring in advance brain activities at a plurality of prescribed regions in a brain of each of a plurality of subjects; the step of generating a discriminator includes the steps of i) calculating, for each of the subjects, a correlation matrix of brain activities among the plurality of prescribed regions from the measured signals; ii) extracting elements of the correlation matrix that connect to a canonical variable corresponding only to a specific attribute information item among the plurality of attribute information items by successively selecting, from M (M: natural number not smaller than 2) different subsets extracted from the plurality of subjects, one subset and performing sparse canonical correlation analysis on the attribute information items and on elements of the correlation matrix of (M-1) subsets except for the selected one subset; iii) obtaining, for the successively selected subsets, a first sum-set as a sum-set of elements of the extracted correlation matrix; and iv) calculating a discriminator for estimating the specific attribute information item from the elements of the first sum-set; the method further including the steps of: storing an information item for specifying the calculated discriminator in the storage device; and performing a process of discriminating input data based on the discriminator specified by the information item stored in the storage device.

According to a still further aspect, the present invention provides a biomarker apparatus, including: a storage device storing information for specifying a discriminator generated by a discriminator generating means from signals obtained by a brain activity detecting means time-sequentially measuring in advance signals representing brain activities at a plurality of prescribed regions in a brain of each of a plurality of subjects; and a discriminating means for performing a process of discriminating input data based on the discriminator specified by the information item stored in the storage device; wherein a plurality of attribute information items are associated to each of the plurality of subjects; the discriminator generating means includes: i) a correlation matrix calculating means for calculating, for each of the subjects, a correlation matrix of brain activities among the plurality of prescribed regions from the measured signals; ii) a first feature extracting means for extracting elements of the correlation matrix that connects to a canonical variable corresponding only to a diagnosis label of a subject among the plurality of attribute information items by successively selecting, from M (M: natural number not smaller than 2) different subsets extracted from the plurality of subjects, one subset and by performing sparse canonical correlation analysis on the attribute information items and on elements of the correlation matrix of (M-1) subsets except for the selected one subset; iii) a first sum-set extracting means for obtaining, for the successively selected subsets, a first sum-set as a sum-set of elements of the extracted correlation matrix; and iv) a discriminator calculating means for generating a discriminator for estimating the diagnosis label of a subject from the elements of the first sum-set.

Preferably, the discriminator calculating means calculates the discriminator for estimating the diagnosis label of a subject from the first sum-set by sparse logistic regression.

Preferably, the discriminator generating means further includes, when subjects other than the above-described M subsets of the plurality of subjects are used as a test set and the test set is divided into N (N: natural number not smaller than 2) different groups, a second feature extracting means for calculating, by sparse logistic regression a test discriminator for estimating the diagnosis label of a subject based on the first sum-set, on a set of subjects except for one group selected from the N groups of the plurality of subjects, and for extracting, along with sparsing, elements of the correlation matrix as the explanatory variables of the test discriminator, and a second sum-set extracting means for iterating feature extraction by the second feature extracting means while successively selecting one group from the N groups for obtaining a second sum-set as the sum-set of elements of the correlation matrix extracted as the explanatory variables of test discriminator; and the discriminator calculating means calculates the discriminator for estimating the diagnosis label of a subject from the second sum-set by sparse logistic regression.

According to a still further aspect, the present invention provides a biomarker apparatus, including: a storage device storing information for specifying a discriminator generated by a discriminator generating device from signals obtained by a brain activity detecting means time-sequentially measuring in advance signals representing brain activities at a plurality of prescribed regions in a brain of each of a plurality of subjects; and a discriminating device for performing a process of discriminating input data based on the discriminator specified by the information item stored in the storage device. A plurality of attribute information items are associated to each of the plurality of subjects. The discriminator is for estimating a diagnosis label of a subject based on the input data. The discriminator generating means includes a processor programmed to: i) calculate, for each of the subjects, a correlation matrix of brain activities among the plurality of prescribed regions from the measured signals; ii) extract elements of the correlation matrix that connect to a canonical variable corresponding only to a diagnosis label of a subject among the plurality of attribute information items by successively selecting, from M (M: natural number not smaller than 2) different subsets extracted from the plurality of subjects, one subset and by performing sparse canonical correlation analysis on the attribute information items and on elements of the correlation matrix of (M-1) subsets except for the selected one subset; iii) obtain, for the successively selected subsets, a first sum-set as a sum-set of elements of the extracted correlation matrix; and iv) generate a discriminator for estimating the diagnosis label of a subject from the elements of the first sum-set.

According to a still further aspect, the present invention provides a computer program causing a computer to execute each of the functions of the above-described biomarker apparatus.

According to a still further aspect, the present invention provides a computer readable storage medium storing any of the above-described programs.

Advantageous Effects of Invention

The present invention realizes a brain activity analyzing apparatus and a brain activity analyzing method that can provide data for objectively determining whether the brain activity is in a healthy or disease state.

Alternatively, the present invention realizes a biomarker apparatus and a program for the biomarker apparatus using brain function imaging, for a neurological/mental disorder.

BRIEF DESCRIPTION OF DRAWINGS

FIG. 19 shows attribute data of subjects at sites A to C.

FIG. 21 shows the attributes of subjects in the United States.

DESCRIPTION OF EMBODIMENTS

Figure 1:
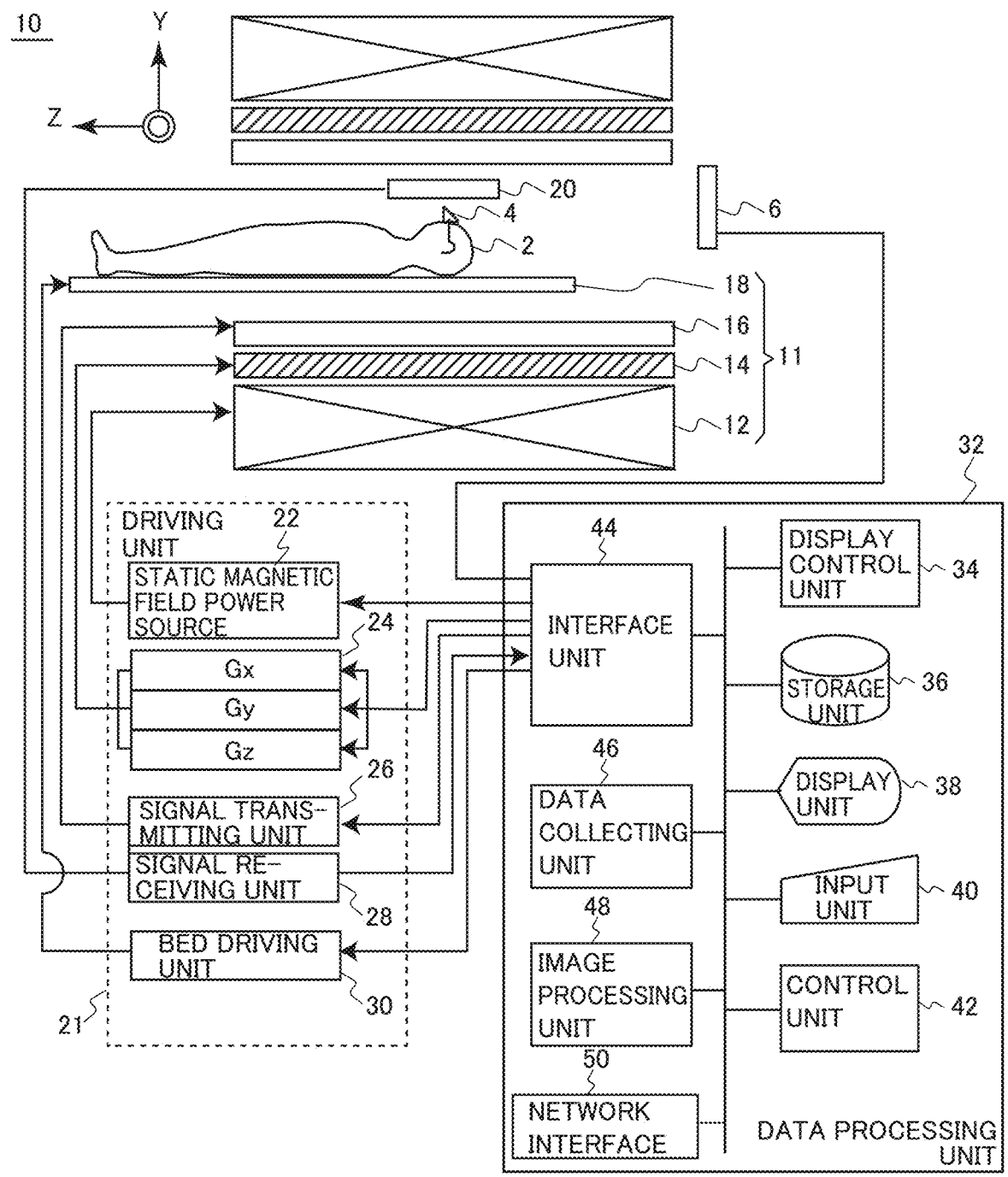
FIG. 1 is a schematic diagram showing an overall configuration of an MRI apparatus 10.

In the following, a configuration of an MRI system in accordance with embodiments of the present invention will be described with reference to the drawings. In the embodiments below, components or process steps denoted by the same reference characters are the same or corresponding components or steps and, therefore, description thereof will not be repeated unless necessary.

First Embodiment

FIG. 1 is a schematic diagram showing an overall configuration of an MRI apparatus 10.

Referring to FIG. 1, MRI apparatus 10 includes: a magnetic field applying mechanism 11 applying a controlled magnetic field to, and irradiating with RF (Radio Frequency) wave, an ROI of a subject 2; a receiving coil 20 receiving a response wave (NMR signal) from subject 2 and outputting an analog signal; a driving unit 21 controlling the magnetic field applied to subject 2 and controlling the transmission/reception of RF wave; and a data processing unit 32 configuring a control sequence of driving unit 21 and processing various data signals to generate an image.

Here, the central axis of a cylindrical bore in which subject 2 is placed is regarded as a Z-axis, and a horizontal direction orthogonal to the Z-axis and the vertical direction orthogonal to the Z-axis are defined as X-axis and Y-axis, respectively.

In MRI apparatus 10 having such a configuration, because of the static magnetic field applied by magnetic field applying mechanism 11, nuclear spins of atomic nuclei forming subject 2 are oriented in the direction of magnetic field (Z-axis) and precess about the direction of magnetic field, with the Larmor frequency unique to the atomic nuclei.

When irradiated with an RF pulse of the same Larmor frequency, the atoms resonate, absorb energy and are excited, resulting in nuclear magnetic resonance (NMR). When the irradiation with RF pulse is stopped after the resonance, the atoms discharge energy and return to the original, steady state. This process is referred to as a relaxation process. In the relaxation process, the atoms output electromagnetic wave (NMR signal) having the same frequency as the Larmor frequency.

The output NMR signal is received by receiving coil 20 as a response wave from subject 2, and the ROIs of subject 2 are imaged by data processing unit 32.

Magnetic field applying mechanism 11 includes a static magnetic field generating coil 12, a magnetic field gradient generating coil 14, an RF irradiating unit 16, and a bed 18 for placing subject 2 in the bore.

By way of example, subject 2 lies on his/her back on bed 18. Though not limited, subject 2 may view an image displayed on a display 6 mounted vertical to the Z-axis, using prism glasses 4. Visual stimulus is applied to subject 2 by an image on display 6. Alternatively, visual stimulus to subject 2 may be applied by projecting an image in front of subject 2 using a projector.

Such a visual stimulus corresponds to the presentation of feedback information in the above-described neurofeedback.

Driving unit 21 includes a static magnetic field power source 22, a magnetic field gradient power source 24, a signal transmitting unit 26, a signal receiving unit 28, and a bed driving unit 30 for moving bed 18 to any position along the Z-axis.

Data processing unit 32 includes: an input unit 40 for receiving various operations and information input from an operator (not shown); a display unit 38 for displaying various images and various pieces of information related to the ROIs of subject 2, on a screen; a display control unit 34 for controlling display unit 38; a storage unit 36 for storing programs, control parameters, image data (structural images and the like) and other electronic data to cause execution of various processes; a control unit 42 controlling operations of various functional units, including generating a control sequence for driving the driving unit 21; an interface unit 44 for executing transmission/reception of various signals to/from driving unit 21; a data collecting unit 46 for collecting data consisting of a group of NMR signals derived from the ROIs; an image processing unit 48 for forming an image based on the data of NMR signals; and a network interface 50 for executing communication with a network.

Data processing unit 32 may be a dedicated computer, or it may be a general purpose computer executing functions causing operations of various functional units, in which designated operations, data processing and generation of control sequence are realized by a program or programs stored in storage unit 36. In the following, description will be given assuming that data processing unit 32 is implemented by a general purpose computer.

Static magnetic field generating coil 12 causes a current supplied from a static magnetic field power source 22 to flow through a helical coil wound around the Z-axis to generate an induction magnetic field, and thereby generates a static magnetic field in the Z-direction in the bore. The ROIs of subject 2 are placed in the region of highly uniform static magnetic field formed in the bore. More specifically, here, static magnetic field generating coil 12 is comprised of four air core coils, forms a uniform magnetic field inside by the combination of the coils, and attains orientation of the spins of prescribed atomic nuclei in the body of subject 2, or more specifically, the spins of hydrogen atomic nuclei.

Magnetic field gradient generating coil 14 is formed of X-, Y- and Z-coils (not shown), and provided on an inner peripheral surface of cylindrical static magnetic field generating coil 12.

These X-, Y- and Z-coils superpose magnetic field gradients on the uniform magnetic field in the bore with the X-axis, Y-axis and Z-axis directions switched in turn, whereby creating intensity gradient in the static magnetic field. When excited, the Z-coil tilts the magnetic field intensity to the Z-direction and thereby defines a resonance surface; the Y-coil applies a tilt for a short period of time immediately after application of the magnetic field in the Z-direction, and thereby adds phase modulation in proportion to the Y-coordinate, to the detected signal (phase encoding); and thereafter the X-coil applies a tilt when data is collected, and thereby adds frequency modulation in proportion to the X-coordinate, to the detected signal (frequency encoding).

The switching of superposed magnetic field gradients is realized as different pulse signals are output to the X-, Y- and Z-coils from the magnetic field gradient power source 24 in accordance with a control sequence. Thus, the position of subject 2 expressed by the NMR can be specified, and positional information in three-dimensional coordinates necessary to form an image of subject 2 are provided.

Here, using the orthogonally crossing three sets of magnetic field gradients, allocating slice direction, phase encoding direction and frequency encoding direction to the magnetic fields respectively, as described above, and by combining these, images can be taken from various angles. By way of example, in addition to transverse slice in the same direction as taken by an X-ray CT apparatus, saggital and coronal slices orthogonal thereto, as well as an oblique slice, of which direction vertical to its plane is not parallel to any of the axes of three orthogonally crossing magnetic field gradients, can be imaged.

RF irradiating unit 16 irradiates ROIs of subject 2 with RF pulses based on a high-frequency signal transmitted from a signal transmitting unit 26 in accordance with a control sequence.

Though RF irradiating unit 16 is built in magnetic field applying mechanism 11 in FIG. 1 it may be mounted on bed 18 or integrated with receiving coil 20.

Receiving, coil 20 detects a response wave (NMR signal) from subject 2, and in order to detect the NMR signal with high sensitivity, it is arranged close to subject 2.

Here, when an electromagnetic wave of NMR signal crosses a coil strand of receiving coil 20, a weak current is generated by electromagnetic induction. The weak current is amplified by signal receiving unit 28 and converted from an analog signal to a digital signal, and then transmitted to data processing unit 32.

The mechanism here is as follows. To a subject 2 in a state of static magnetic field with Z-axis magnetic field gradient added, a high-frequency electromagnetic field of resonance frequency is applied through RF irradiating unit 16. Prescribed atomic nuclei, for example, hydrogen atomic nuclei, at a portion where magnetic field intensity satisfies the condition of resonance are selectively excited and start resonating. Prescribed atomic nuclei at a portion satisfying the condition of resonance (for example, a slice of prescribed thickness of subject 2) are excited, and spin axes concurrently start rotation. When the excitation pulse is stopped, electromagnetic waves irradiated by the spin axes in rotation induce a signal in receiving coil 20 and, for some time, this signal is continuously detected. By this signal, a tissue containing the prescribed atoms in the body of subject 2 is monitored. In order to know the position where the signal comes from, X- and Y-magnetic field gradients are added and the signal is detected.

Based on the data built in storage unit 36, image processing unit 48 measures detected signals while repeatedly applying excitation signals, reduces resonance frequency to X-coordinate by a first Fourier transform to obtain an image, restores Y-coordinate by a second Fourier transform, and thus, displays the corresponding image on display unit 38.

For example, by picking-up the NMR signal corresponding to the above-described BOLD effect on a real-time basis using the MRI system as described above and performing an analysis, which will be described later, on the time-sequentially picked-up images by control unit 42, it is possible to take images of the resting-state functional connection MRI (rs-fcMRI).

Figure 2:
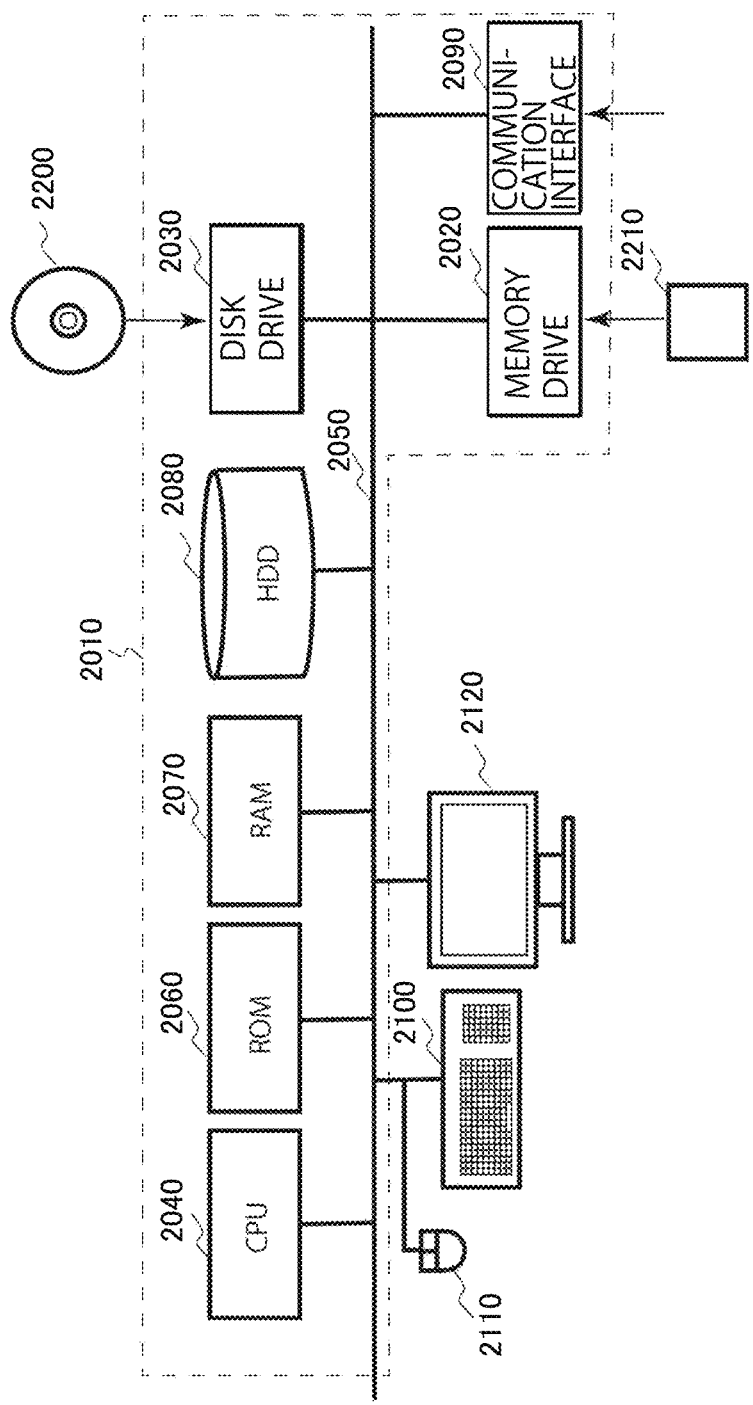
FIG. 2 is a hardware block diagram of data processing unit 32.

FIG. 2 is a hardware block diagram of data processing unit 32.

Though the hardware of data processing unit 32 is not specifically limited as described above, a general-purpose computer may be used.

Referring to FIG. 2, a computer main body 2010 of data processing unit 32 includes, in addition to a memory drive 2020 and a disk drive 2030, a processor (CPU) 2040, a bus 2050 connected to disk drive 2030 and memory drive 2020, an ROM 2060 for storing programs such as a boot-up program, an RAM 2070 for temporarily storing instructions of an application program and providing a temporary memory space, a non-volatile storage device 2080 for storing application programs, system programs and data, and a communication interface 2090. Communication interface 2090 corresponds to an interface unit 44 for transmitting/receiving signals to/from driving unit 21 and the like and a network interface 50 for communicating with another computer through a network, not shown. As non-volatile storage device 2080, a hard disk, a solid state drive or the like may be used. Non-volatile storage device 2080 corresponds to storage unit 36 shown in FIG. 1.

By operation processes executed by CPU 2040 in accordance with a program, various functions of data processing unit 32 including, for example, functions of control unit 42, data collecting unit 46 and image processing unit 48 are realized.

A program or programs causing data processing unit 32 to execute the function of the present embodiment as described above may be stored in a CD-ROM 2200 or a memory medium 2210 and inserted to disk drive 2030 or memory drive 2020 and may be further transferred to non-volatile storage device 2080. The program or programs will be loaded to RAM 2070 before execution.

Data processing unit 32 further includes a keyboard 2100 and a mouse 2110 as input devices, and a display 2120 as an output device. Keyboard 2100 and mouse 2110 correspond to input unit 40 and display 2120 corresponds to display unit 38.

The program or programs realizing the functions of data processing unit 32 as described above may not necessarily include an operating system (OS) for executing the functions of information processing apparatus such as computer main body 2010. The program or programs may only include those portions of instructions which can call appropriate functions (modules) in a controlled manner to attain a desired result. The manner how data processing unit 32 operates is well known and, therefore, detailed description will not be given here.

Further, the above-described program or programs may be executed by one computer or by a plurality of computers. In other words, both centralized processing and distributed processing are possible.

Figure 3:
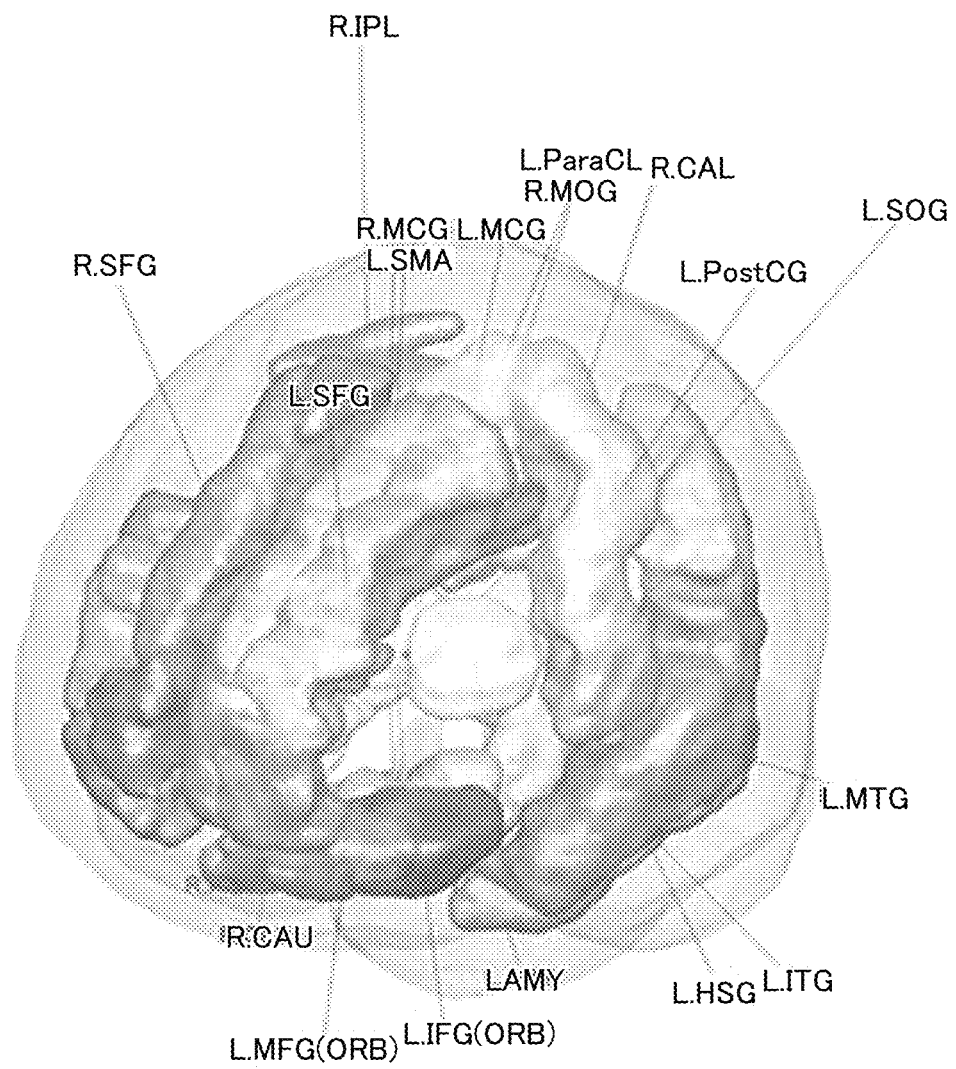
FIG. 3 shows regions of interest (ROIs) of a brain imaged by rs-fcMRI in accordance with an embodiment.

FIG. 3 shows ROIs of a brain imaged by rs-fcMRI in accordance with the present embodiment.

Here, a biomarker related to Autistic Spectrum Disorder (ASD) will be described as an example, and 140 regions are used as ROIs.

Such ROIs include, by way of example, the following:
Dorsomedial Prefrontal Cortex (DMPFC);
Ventromedial Prefrontal Cortex (VMPFC);
Anterior Cingulate Cortex (ACC);
Cerebellar Vermis:
Left Thalamus:
Right Inferior Parietal Lobe;
Right Caudate Nucleus;
Right Middle Occipital Lobe; and
Right Middle Cingulate Cortex.

It is noted, however, that the brain regions used may not be limited to those above.

For instance, the regions to be selected may be changed in accordance with the neurological/mental disorder to be studied.

Figure 4:
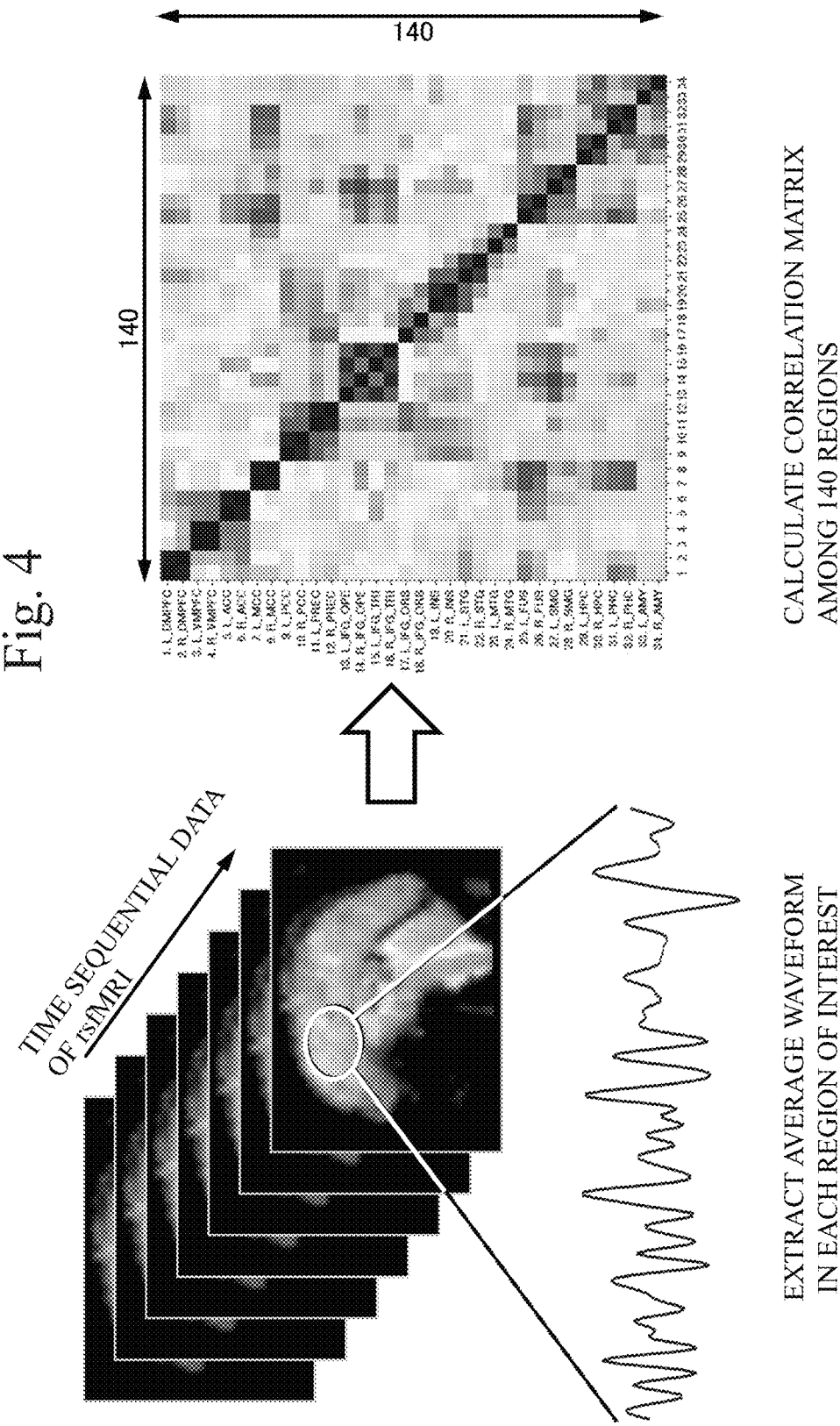
FIG. 4 shows a concept of a procedure for extracting a correlation matrix representing correlations of functional connection of ROIs in the resting state.

FIG. 4 shows a concept of a procedure for extracting a correlation matrix representing correlations of functional connections in the resting state, from ROIs such as shown in FIG. 3.

Referring to FIG. 4, from fMRI data of n (n: a natural number) time points in the resting state measured on a real-time basis, an average "degree of activity" of each region of interest is calculated, and correlations among the brain regions (among the ROIs) are calculated.

Here, 140 regions are picked up as ROIs as noted above and, therefore, the number of independent non-diagonal elements in the correlation matrix will be, considering the symmetry, (140×140−140)/2=9730.

In FIG. 4, only the correlations of 34×34 are shown.

Though not specifically limited, calculation of such elements of a correlation matrix may be executed in the following manner.

From the data of brain activities in the resting state, for each subject, Functional Connections (FC) among different ROIs are calculated. FC is a feature generally used in analyzing brain activity in the resting state, and it is defined by Pearson's correlation coefficient between different ROI time-sequential signals.

First, time sequence of mean signals of all voxels included in each ROI is extracted.

Thereafter, band-pass filtering is conducted for noise cancellation of signal values, followed by regression using nine explanatory variables (mean signals of whole brain, white matter, brain spinal fluid and six motion correction parameters).

Residual error sequence after regression is regarded as a time-sequential signal values related to functional connections, and Pearson's correlation coefficient is calculated among time sequences of different ROIs.

As for ROIs, in addition to 137 ROIs included in Brain Sulci Atlas (BAL), cerebellums (left and right) and vermis of Automated Anatomical Labeling Atlas are used. Functional connections (FC) among these 140 ROIs are used as features.

Here, Brain Sulci Atlas (BAL) and Automated Anatomical Labeling Atlas are disclosed in the following references.
Reference: Perrot et al., Med Image Anal, 15 (4), 2011
Reference: Tzourio-Mazoyer et al, Neuroimage, 15 (1), 2002

Figure 5:
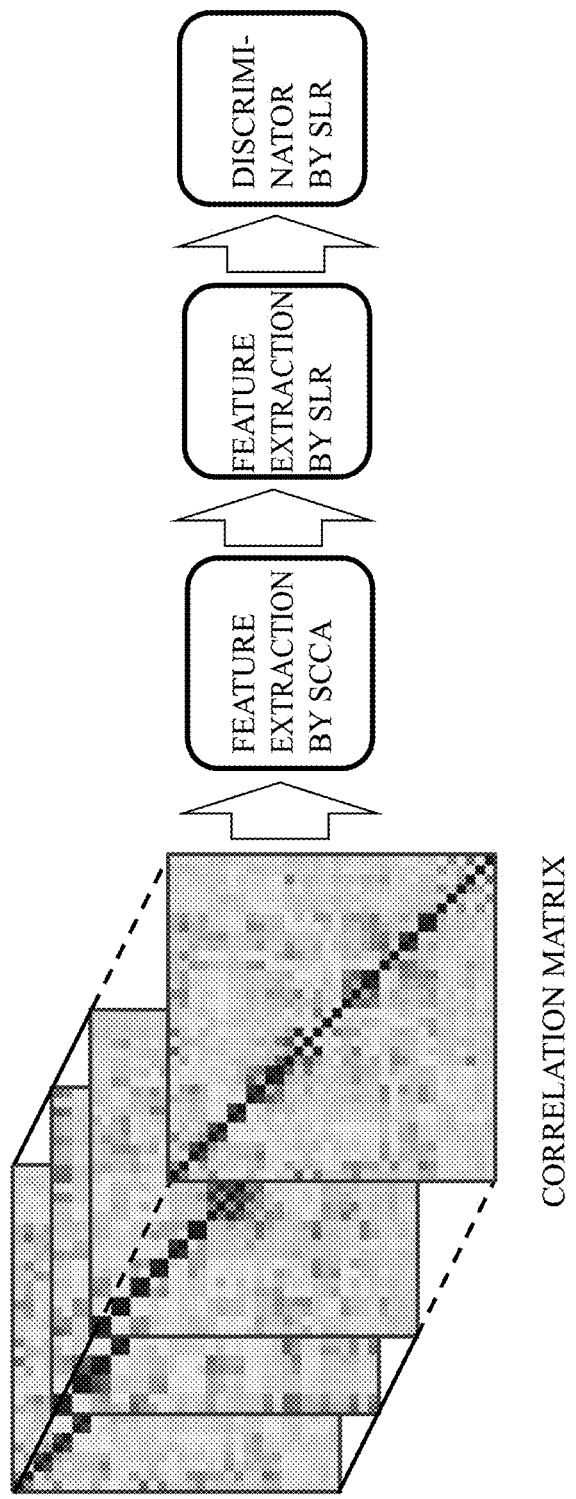
FIG. 5 shows a concept of a process for generating a discriminator serving as a biomarker, from the correlation matrix.

FIG. 5 shows a concept of a process for generating a discriminator serving as a biomarker, from the correlation matrix described with reference to FIG. 4.

Referring, to FIG. 5, from data of resting-state functional connection MRI obtained by measuring a group of healthy subjects and a group of patients, data processing unit 32 derives a correlation matrix of degrees of activities among brain regions (ROIs) in accordance with a procedure that will be described later.

Thereafter, by data processing unit 32, feature extraction is performed by regularized canonical correlation analysis on the correlation matrix and on the attributes of subjects including disease/healthy labels of the subjects. Here, "regularization" generally refers to a method of preventing over-learning by adding a regularization term weighted by hyper parameters to an error function, in machine learning and statistics, and thereby restricting complexity/degrees of freedom of a model. If the result of regularized canonical correlation analysis results in sparse explanatory variables, this process will be specifically referred to as a sparse canonical correlation analysis (SCCA). In the following, an example employing sparse canonical correlation analysis will be described.

In sparse canonical correlation analysis as such, when hyper parameter values are adjusted to allow presence of a canonical variable that connects only to a "diagnosis label" as will be described later, a functional connection FC that connects to the corresponding canonical variable is extracted. When the hyper parameters are varied in a prescribed range, a sum-set of functional connections FC extracted in a range in which the canonical variables satisfying such conditions exist will be referred to as a "first sum-set."

Further, using the "first sum-set" obtained as a result of sparse regularized canonical correlation analysis, data processing unit 32 performs Leave-One-Out Cross Validation: LOOCV) while performing discrimination analysis by sparse logistic regression at each step of cross validation, whereby a sum-set of functional connections FC are extracted as explanatory variables over all the cross validations, which set will be referred to as a "second sum-set."

Finally, the data of all subjects are subjected to discrimination analysis by sparse logistic regression of "diagnosis label" as the object variable, using the "second sum-set" as explanatory variables, and thus, a discriminator is generated.

As will be described later, the data of healthy group and the patient group are not limited to those measured by the MRI apparatus 10 itself. Data measured by a different MRI apparatus may also be integrated, to generate the discriminator. More generally, data processing unit 32 may not necessarily be a computer for executing control of the MRI apparatus, and it may be a computer specialized in generating the discriminator by receiving measurement data from a plurality of MRI apparatuses and performing the discriminating process by using the generated discriminator.

Figure 6:
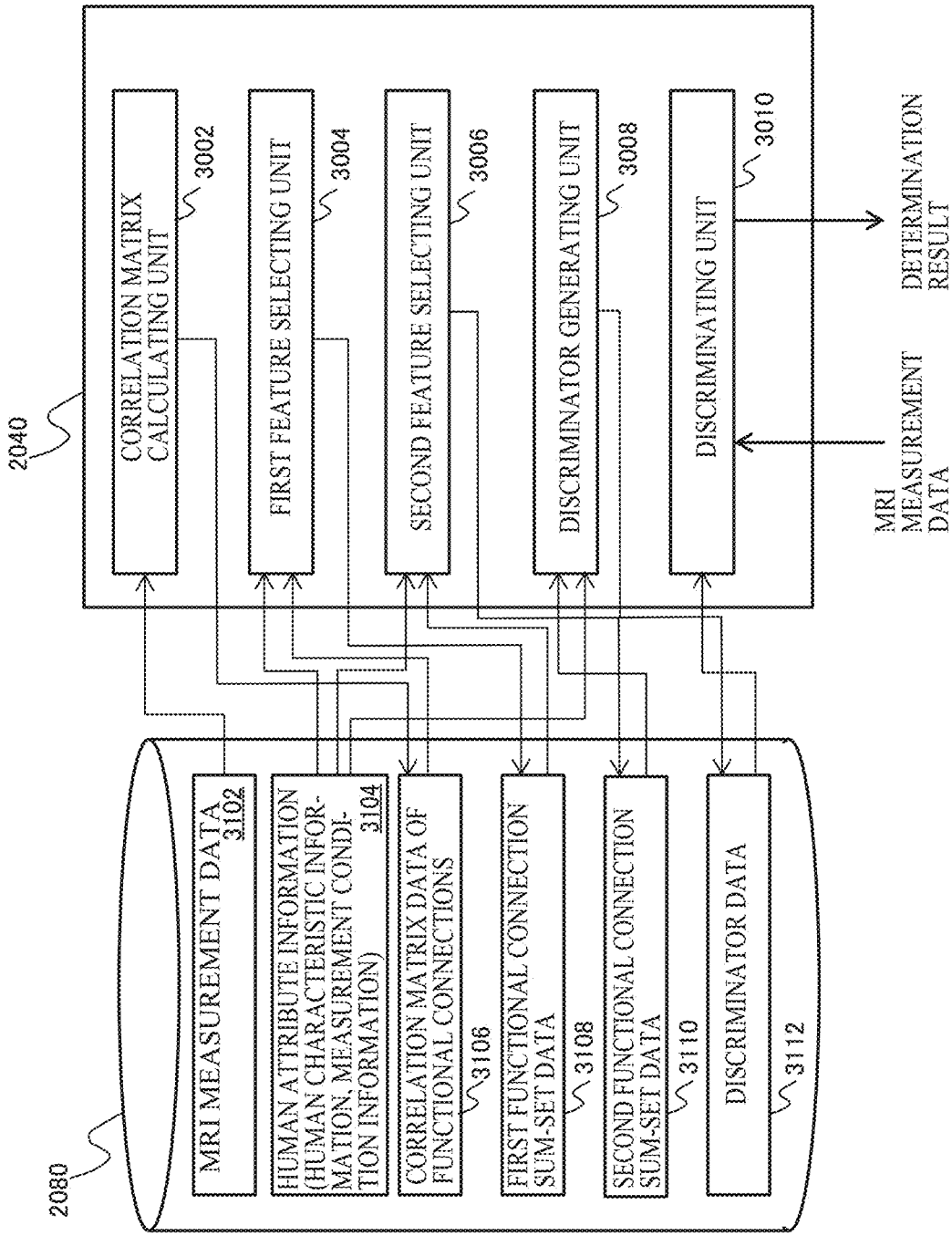
FIG. 6 is a functional block diagram for a discriminator generating process such as shown in FIG. 5 and a discriminating process by the generated discriminator.

FIG. 6 is a functional block diagram for a discriminator generating process such as shown in FIG. 5 and a discriminating process by the generated discriminator.

First, a non-volatile storage device 2080 stores MRI measurement data 3102, which is information of signals measured time-sequentially in advance by the MRI device as signals representing brain activities in a prescribed plurality of regions in the brain of each of the subjects; and pieces of human attribute information 3104 associated with each of the subjects whose MRI measurement data are measured.

Here, "human attribute information" includes pieces of "human characteristic information" for specifying individual subject and "measurement condition information" for specifying measurement conditions for each subject.

"Human characteristic information" means information such as diagnosis label, age, sex, medication profile and the like of each subject.

"Measurement condition information" includes information of measurement site where measurement of the subject took place (including information specifying the measurement facility and/or device used for measurement) and conditions such as whether the eyes were open/closed during measurement, as well as conditions for measurement such as magnetic field strength for measurement.

Processor 2040 performs the process of generating a discriminator for the diagnosis label based on the MRI measurement data 3102 and the corresponding human attribute information 3104.

A correlation matrix calculating unit 3002 calculates, for each subject, the correlation matrix of functional connection of brain activities among a prescribed plurality of regions from the MRI measurement data 3102. The data of the correlation matrix of functional connection is stored, subject by subject, as correlation matrix data 3106 of functional connection, in non-volatile storage device 2080.

A first feature selecting unit 3004 successively selects, from K (K: a natural number not smaller than 2) different subsets extracted from a plurality of subjects, one subset and performs a sparse canonical correlation analysis on pieces of attribute information and on elements of the correlation matrix of (K-1) subsets except for the selected one subset, and thereby extracts elements of a correlation matrix that connects to a canonical variable corresponding only to a specific piece of attribute information among the pieces of human attribute information, for example, the diagnosis label. Further, the first feature selecting unit 3004 obtains, for the successively selected subsets, the first sum-set as the sum-set of extracted elements of correlation matrix, and stores as first functional connection sum-set data 3108 in non-volatile storage device 2080. Here, the "first functional connection sum-set data" may be indices for specifying elements corresponding, to the first sum-set, among the functional connection correlation matrix data 3106.

Subjects other than the above-described K subsets of the plurality of subjects are used as a test set, which test set is divided into N different groups; the second feature selecting unit 3006 calculates by sparse logistic regression a test discriminator for estimating the above-described specific attribute information (for example, the diagnosis label) based on the first sum-set, on a set of subjects except for one group selected from the N groups of the plurality of subjects; and extracts, along with sparsing, elements of the correlation matrix as the explanatory variables of the test discriminator. Further, the second feature selecting unit 3006 repeats feature extraction while successively selecting one group from N groups to obtain the second sum-set as the sum-set of elements of the correlation matrix extracted as the explanatory variables of test discriminator, and stores it as the second functional connection sum-set data 3110 in non-volatile storage device 2080. Here again, the "second functional connection sum-set data" may be indices for specifying elements corresponding to the second sum-set among the functional connection correlation matrix data 3106.

It is noted that the number of elements in each of the N groups may be one.

A discriminator generating unit 3008 calculates by the sparse logistic regression a discriminator for estimating a specific attribute information (for example, the diagnosis label) using the second sum-set as explanatory variables. Discriminator generating unit 3008 stores information for specifying the generated discriminator as discriminator data 3112 in non-volatile storage device 2080.

A discriminating unit 3010 performs a discriminating process on input data based on the discriminator specified by discriminator data 3112.

In the description above, discriminator generating unit 3008 has been described as generating a discriminator using the second sum-set as explanatory variables. Alternatively, discriminator generating unit 3008 may generate a discriminator by directly using the first sum-set as the explanatory variables. From the viewpoint of reducing the number of dimensions and of improving generalization, however, it is desirable to use the second sum-set as the explanatory variables.

In generating a discriminator, it is possible to use regularized logistic regression, which is logistic regression with regularization (for example, L1 regularization or L2 regularization). More specifically, the above-described "sparse logistic regression" may be used. Further, for generating a discriminator, a support vector machine or LDA (linear discriminant analysis) may be used. In the following, an example using sparse logistic regression will be described.

As will be described later, in parallel with the feature selecting process by the second feature selecting unit 3006, using the test discriminator calculated by the second feature selecting unit 3006, while successively selecting one group to be excluded from the N groups, the excluded group may be used as a test sample and the result of discrimination may be calculated, and whereby cross-validation may be effected.

By reducing the dimension of explanatory variables by the nested feature selecting procedure, it becomes possible to realize time-efficient reduction of the number of dimensions, while using the data of almost all subjects, in the process performed by the second feature selecting unit 3006.

Further, by making the test set in the process of second feature selecting unit 3006 independent from the data set used for reducing the number of dimensions, it becomes possible to avoid excessively optimistic results.

Figure 7:
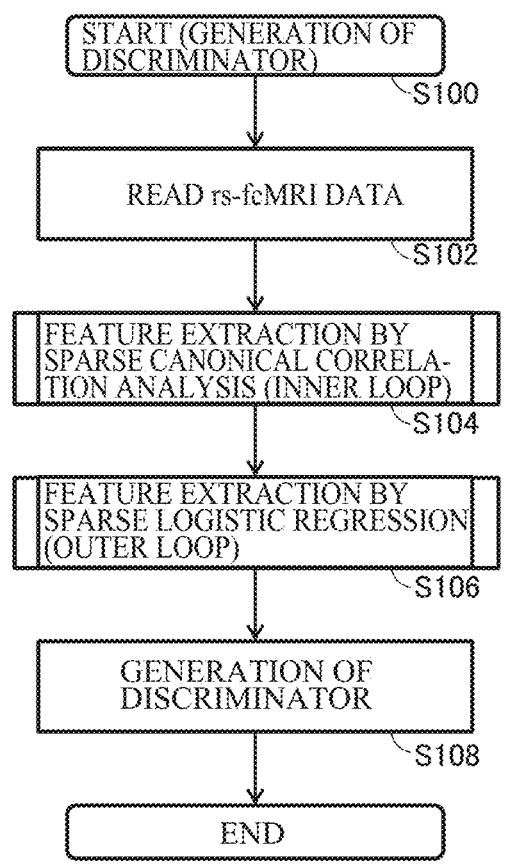
FIG. 7 is a flowchart representing a process executed by data processing unit 32 for generating the discriminator serving as the biomarker.

FIG. 7 is a flowchart representing a process executed by data processing unit 32 for generating the discriminator serving as the biomarker.

In the following, the process described with reference to FIG. 5 will be discussed in greater detail with reference to FIG. 7.

The biggest problem posed when a biomarker is to be generated based on the discriminant label (diagnosis label) of a disease of a subject and connections of brain regions derived from the fMRI data in the resting state is that the number of data dimensions is overwhelmingly larger than the number of data. Therefore, if training of a discriminator for predicting the diagnosis label (here, the label indicating whether the subject has the disease or healthy will be referred to as the "diagnosis label") is done using a data set without regularization, the discriminator will be over-fitted, and the prediction performance for unknown data significantly decreases.

Generally, in machine learning, a process to enable explanation of observed data with a smaller number of explanatory variables is referred to as "feature selection (or feature extraction)." In the present embodiment, "extraction of contraction expression" refers to feature selection (feature extraction) to enable formation of the discriminator with smaller number of correlation values in the machine learning of the discriminator for predicting the diagnosis label of a disease to be studied from among "a plurality of correlation values (a plurality of connections) of the degrees of activities among the brain regions (regions of interest: ROIs)," that is, to select correlation values of higher importance as the explanatory variables.

In the present embodiment, as the method of feature extraction, regularization is adopted. In this manner, canonical correlation analysis is performed with regularization and sparsintz, so as to leave explanatory variables of higher importance. This process is referred to as "sparse canonical correlation analysis." More specifically, as the method of regularization that also realizes sparsing, we can use a method of imposing a penalty to the magnitudes of absolute values of parameters for canonical correlation analysis referred to as "L1 regularization" as will be described in the following.

Specifically, referring to FIG. 7, when the process for generating the discriminator starts (S100), data processing unit 32 reads MRI measurement data of each subject from storage unit 36 (S102), and performs the first feature extraction process by the sparse canonical correlation analysis (S104).

In the following, the process at step S104 will be referred to as "inner loop feature selection."

Here, in order to facilitate understanding of the inner loop feature selection process at step S104, the "sparse canonical correlation analysis" and the "inner loop feature selection" will be described.

(Sparse Canonical Correlation Analysis)

In the following, L1 regularization canonical correlation analysis will be described as the sparse canonical correlation analysis. As to the L1 regularization canonical correlation analysis, see, for example, the reference below.

Reference: Witten D M, Tibshirani R, and T Hastie. A penalized matrix decomposition, with applications to sparse principal components and canonical correlation analysis. Biostatistics, Vol. 10, No. 3, pp. 515-534, 2009.

First, in the general Canonical Correlation Analysis (CCA), when a variable pair $x_1$ and $x_2$ is to be considered. the variables $x_1$ and $x_2$ are each standardized to have an average zero and standard deviation one.

Generally speaking, by using the canonical correlation analysis, it becomes possible to identify the latent relation between paired observables.

Specifically, in the canonical correlation analysis, a projection vector is found such that projected pair of variables (canonical variables) have the highest correlation.

In contrast, when the L1 regularization is introduced to the canonical correlation analysis, that is, when the sparse CCA with L1 norm regularization or L1-SCCA is used, the process will be to solve the following optimization problem.

Consider the following sets of variables.

Where there are N sets of observed values of variables, $X_1 = [x_1^1, x_1^2, \Lambda\, x_1^N]^T$ represents a N×p1 matrix comprised of a first set of variables, and $X_2 = [x_2^1, x_2^2, \Lambda\, x_2^N]^T$ represents N×p2 matrix comprised of a second set of variables.

Here again, it is assumed that the columns forming matrices $X_1$ and $X_2$ are each normalized to have an average zero and variance one.

Then, L1-SCCA can be formulated as Equation (1) below.

$$\max_{w_1, w_2} w_1^T X_1^T X_2 w_2 \text{ subject to} \tag{1}$$

$$\|w_1\|_1^2 \le \lambda_1, \|w_2\|_1^2 \le \lambda_2, \|w_1\|_2^2 \le 1, \|w_2\|_2^2 \le 1$$

Here, hyper parameters $\lambda_1$ and $\lambda_2$ respectively represent the degrees of sparseness (referred to as "sparse projection vectors" because the variables corresponding to $w_1$ and $w_2$ are made sparse) of weight parameters $w_1$ and $w_2$.

Specifically, in the present embodiment, in order to identify the latent relations of the functional connections FC and the human attribute information, two data matrixes corresponding to the above-described variables are formed.

In the following, the subjects include a group of autism patients (whose diagnosis label is indicated as "ASD (Autism Spectrum Disorder)" and a group of typically developing people (whose diagnosis label is indicated as "TD (Typically Developing)". The column of the first data matrix $X_1$ represents the human attribute information (human characteristic information and measurement condition information) of one subject, and the characteristic information and measurement condition information include the following:

i) diagnosis label (ASD or TD)
ii) site information (at which site the brain activities of the subject were measured, site A, B or C)
iii) age
iv) sex
v) conditions of imaging (eyes open or closed)
vi) state of first medication (antipsychotic medicine)
vii) state of second medication (antidepressant)
viii) state of third medication (tranquillizer)

Specifically, the number of columns of the human attribute information data matrix $X_1$ is 10, that is, $p_1$=10.

The first column includes 1 (=ASD) or 0 (=TD).

The following three columns indicate facilities (sites) where the brain activities were measured and, in this example, these columns include any of [100] (site A), [010] (site B) and [001] (site C), corresponding to measurements that took place at three different sites.

The fifth column includes a value indicating, the age of the subject; the sixth column represents information of the sex of the subject, and it includes either the value 1 (male) or 0 (female); the seventh column indicates, among the conditions of measurement, whether the subject's eyes were open or closed during the measurement, and it includes the value 1 (eyes open) or 0 (eyes closed). The last three columns includes status information related to medication profile of three medicines and each column includes a value 1 (medicine administered) or 0 (medicine not administered), respectively.

The human characteristic information and the measurement condition information are not limited to those described above. For example, other characteristics such as information of medical profile related to other medicines of the subjects, or other conditions of measurement such as the magnitude of magnetic field applied by the MRI apparatus, may be included.

The second data matrix $X_2$ represents, in the form of a row vector, elements at the off-diagonal lower triangle of the correlation matrix representing the correlation of the functional connections (FC) of the subject.

Then, L1-SCCA is applied to the pair of matrices $X_1$ and $X_2$, and thereby, sparse projection vectors $w_1$ and $w_2$ are derived.

Then, as described above, the following conditions are set to be satisfied: specifically, when the hyper parameters $\lambda_1$ and $\lambda_2$ are set to prescribed values, the first data matrix $X_1$ will be projected, by the sparse projection vector $w_1$, through sparsing, to a canonical variable representing only a specific piece of human attribute information: "diagnosis label" in this case. Here, in the corresponding second data matrix $X_2$, in order to specify an index (element) for identifying the element of the correlation matrix of that functional connection which relates only to the diagnosis label, the sparse projection vector $w_2$ is used.

Specifically, in the inner loop feature selection, hyper parameters $\lambda_1$ and $\lambda_2$ of L1-SCCA are changed independently between 0.1 and 0.9 at a step of, for example, 0.1.

The range and the magnitude of the steps of changing the hyper parameters $\lambda_1$ and $\lambda_2$, however, are not limited to such examples.

For the process of L1-SCCA, the range of hyper parameters $\lambda_1$ and $\lambda_2$ in which such a canonical variable that is connected only to the "diagnosis" label exists, should be found.

Under the conditions of experiment as will be described later, the combinations of $\lambda$ satisfying this condition of constraint were, in average, 17.6±5.0% of 45 overall possible combinations in the example above.

Here, projection of elements of the original correlation matrix to a subspace defined by non-zero elements of derived sparse projection vector $w_2$ is represented as follows.

Here, a variable $i_k$ is defined to indicate an index of a k-th non-zero element of the sparse projection vector $w_2$. Here, $1 \leq k \leq m$, and m represents the number of non-zero elements.

Then, consider a projection matrix E to a subspace as below.

$$E=[e_{i_1}, e_{i_2}, \Lambda e_{i_m}]^T$$

Here, $e_{i_k} \in R^{P2}$ is a standard basis vector including "1" in the ik-th element and "0" in another element.

Finally, by projecting the element $x_2$ of the original correlation matrix in the following manner, a vector to the subspace $z \in R^m$ is derived.

$$z=Ex_2 \quad (2)$$

As a result, it is possible to select a specific number of features (elements of the correlation matrix) that relate to the diagnosis label (ASD/TD).

By selecting elements of the correlation matrix that correspond to the canonical variables related only to the diagnosis label, elements of the correlation matrix that are essential to classification can be selected.

(Inner Loop Feature Extraction)

Figure 8:
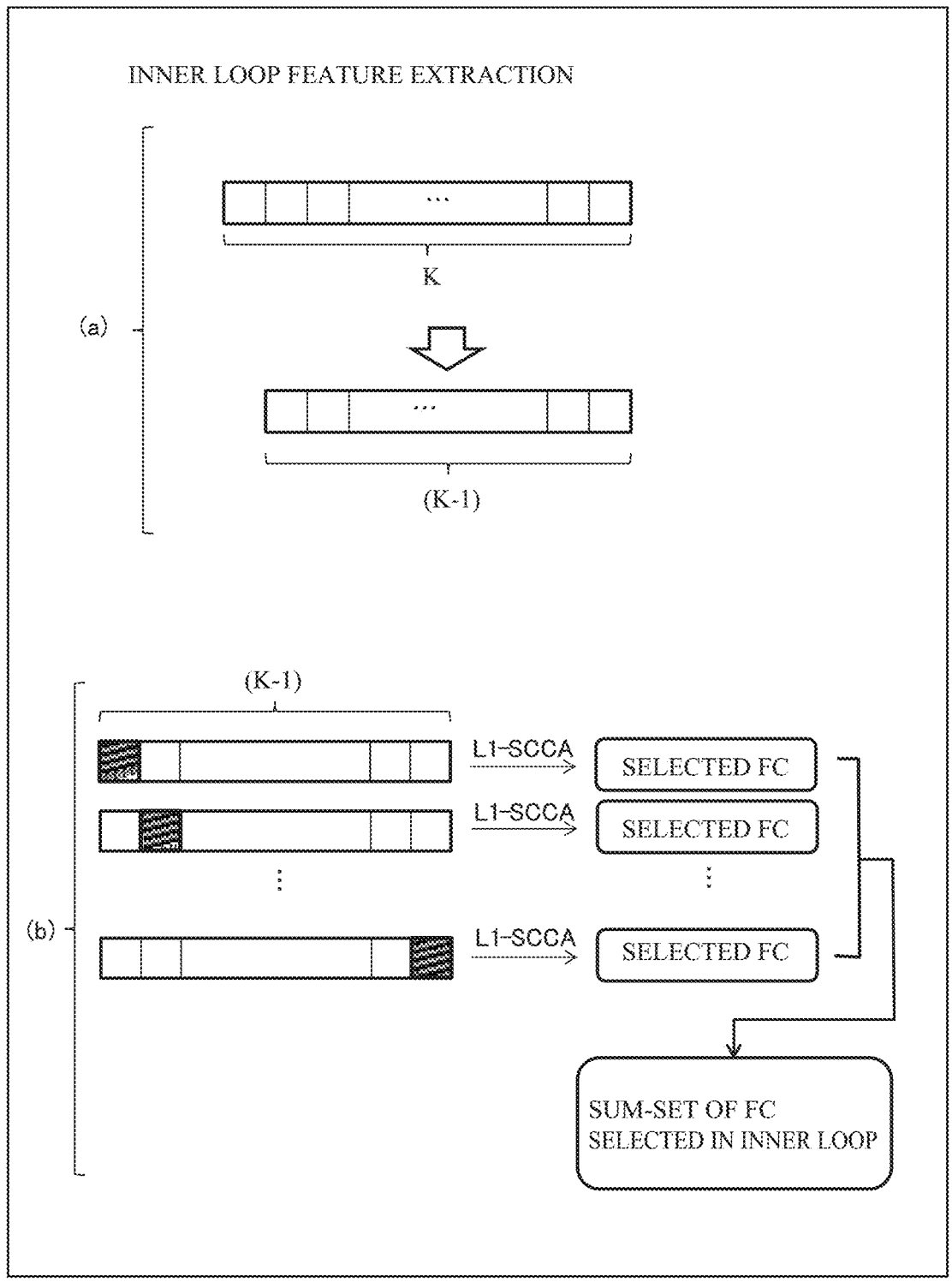
FIG. 8 includes schematic diagrams showing an inner loop feature selection.

FIG. 8 includes schematic diagrams showing an inner loop feature selection.

The inner loop feature selection at step S104 of FIG. 7 is as follows: as shown in FIG. 8, a set of subjects is divided into K subsets (K: an integer not smaller than 2), and of (K-1) subsets, subsets except for one is subjected to L1-SCCA and this process is repeated for (K-1) times.

Specifically, referring to FIG. 8(a), a subset (hereinafter referred to as "inner loop training data") corresponding to (K-1)/K (for example, if K=9, 8/9) of the set of subjects is used for the inner loop feature selection as such. The remaining one of the K subsets is used as a "test pool" including test data as the object of training in an outer loop feature selection, which will be described later, and hence, it is not used in the inner loop feature selection.

As shown in FIG. 8(b), of the (K-1) subsets, one set (hatched in FIG. 8(b)) is excluded and the remaining subsets are subjected to L1-SCCA with hyper parameters $\lambda_1$ and $\lambda_2$ changed stepwise in a prescribed range. Elements of functional connection FC related to canonical variables related only to the "diagnosis" label are extracted as features within a specific range of hyper parameters $\lambda_1$ and $\lambda_2$.

The extracting process as described above is iterated on the (K-1) subsets with one set to be excluded therefrom switched successively.

A sum-set of extracted elements FC of the correlation matrix of the functional connections will be referred to as a "sum-set of elements of functional connections FC selected in an inner loop" (first sum-set).

By this process, undesirable influence caused by differences in human attribute information at different imaging sites or differences in imaging conditions at different imaging sites, corresponding to noise variables NV, can be reduced.

This procedure will be helpful when a discriminator generated based on MRI measurement data from imaging sites in Japan is to be robustly generalized abroad, for example, in the United States.

Again referring to FIG. 7, thereafter, data processing unit 32 executes the second feature extraction process (S106) using the sparse logistic regression based on the results of the inner loop feature selection.

In the following, the process at step S106 will be referred to as "an outer loop feature selection."

Here, in order to facilitate understanding of the outer loop feature selection process at step S106, the "sparse logistic regression" and the "outer loop feature selection" will be described, respectively, in the following.

(Sparse Logistic Regression)

The sparse logistic regression refers to a method of a logistic regression analysis expanded to a Bayes' estimation scheme, in which dimensional compression of a feature vector is performed concurrently with weight estimation for discrimination. This is useful when the feature vector is in a very large dimension and includes many unnecessary feature elements. For unnecessary feature elements, weight parameter in linear discrimination analysis will be set to zero (that is, feature selection is done), so that only a limited number of feature elements related to the discrimination are extracted (sparseness).

In the sparse logistic regression, the probability p of the obtained feature data belonging to a class is calculated class by class, and the feature data is classified to the class corresponding to the highest output value. The value p is output by a logistic regression equation. Weight estimation is done by ARD (Automatic Relevance Determination), and feature elements with little contributing to class determination are removed from the calculation as its weight comes closer to zero.

Specifically, using the first sum-set of features extracted by the L1 regularization CCA as described above as inputs, the discriminator based on the hierarchical Bayes' estimation as will be described in the following estimates the diagnosis label.

Here, in order to predict the probability of the diagnosis label indicating a disease (here, diagnosis of autism) from the feature input z (selected FC) extracted by Equation (2) above, logistic regression is utilized as a discriminator.

$$p(y=1\mid\theta) = \frac{1}{1+\exp(-\theta^T\hat{z})} \quad (3)$$

Here, y represents diagnosis class/label. Specifically, y=1 represents the ASD class and y=0 represents the TD class.

Further, the following z hat (a character with "∧" above will be referred o as "hat") represents a feature vector with an extended input.

$$\hat{z} = [z^T, 1]^T \in R^{m+1}$$

Here, the feature vector z is extracted in accordance with Equation (2) from the connection correlation matrix of MRI samples of one subject in a resting state.

Use of extended input "1" is a standard approach for introducing a certain (bias) input to the discriminator.

θ shown in the following is a parameter vector of a logistic function.

$$\theta \in R^{m+1}$$

Here, the distribution of parameter θ is set to a normal distribution given as $$p(\theta\mid\alpha) = N(\theta\mid 0, \text{diag}(\alpha))$$

Further, by setting the distribution of hyper parameter α of distribution of parameter w as follows, distribution of each parameter is estimated by hierarchical Bayes' estimation.

$$p(\alpha) = \prod_j \Gamma(\alpha_i \mid a^0, b^0)$$

Here, $a^0$ and $b^0$ are parameters determining gamma distribution of hyper parameter. α is a parameter vector representing variance of normal distribution of vector θ, and the i-th element of vector α is represented by $\alpha_i$.

As to the sparse logistic regression, see, for example, the following reference.

Reference: Okito Yamashita, Masaaki Sato, Taku Yoshioka, Frank Tong, and Yukiyasu Kamitani. "Sparse Estimation automatically selects voxels relevant for the decoding of fMRI activity patterns." NeuroImage, Vol. 42, No. 4, pp. 1414-1429, 2008.

(Outer Loop Feature Selection)

Figure 12:
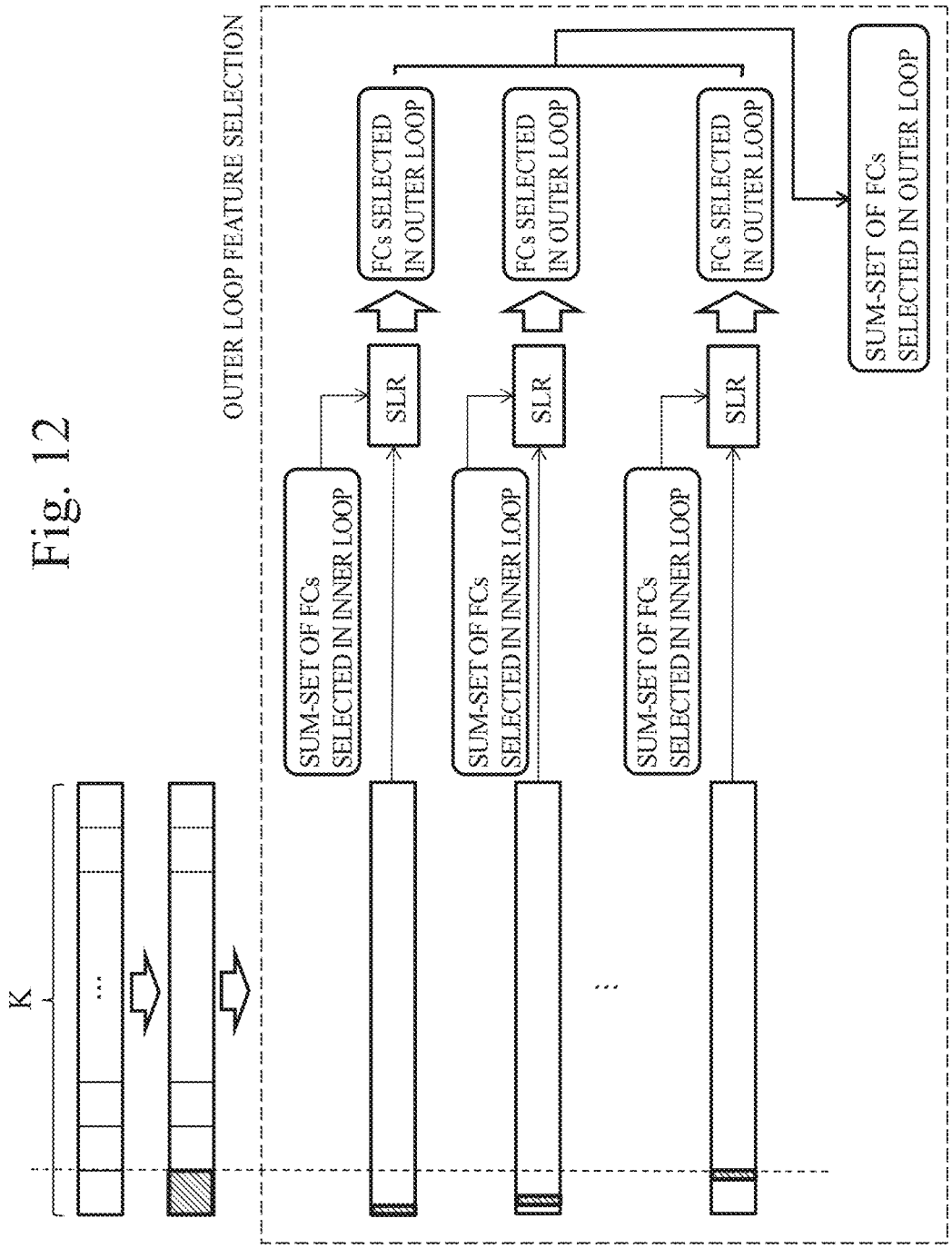
FIG. 12 is a schematic diagram showing an outer loop feature selection.

FIG. 12 is a schematic diagram showing an outer loop feature selection.

The outer loop feature selection at step S106 of FIG. 7 is as follows: as shown in FIG. 12, a set of subjects is divided into K subsets (K: an integer not smaller than 2), and one subset other than the (K-1) subsets used for the inner loop feature selection is used as a "test pool" including test data as the object of training.

Specifically, referring to FIG. 12, the test pool is divided into L groups, and each group (hatched in the rectangle divided by a dotted line in FIG. 12) in turn is selected from the L groups. Then, for the set of subjects except for this selected group, a discriminator for predicting the diagnosis label is generated by the sparse logistic regression, using the elements FC of the correlation matrix of functional connections or the first sum-set as the explanatory variable. Here, by the sparse logistic regression, the "elements FC of the correlation matrix of functional connections" is further selected. This will be referred to as "elements FC of the correlation matrix of functional connections selected in the outer loop."

By selecting one group each in turn from L groups in this manner and by iterating such a process L times, a sum-set of extracted elements FC of correlation matrix of functional connections is obtained, which is referred to as "sum-set of elements of functional connection FC selected in an outer loop" (second sum-set).

As described above, the test set used for outer loop feature extraction is always independent from the data set used for reducing the number of dimensions in the inner loop feature extraction.

Here, as an example, it is assumed that each of L groups includes one subject. Thus, in the iteration mentioned above, performing the prediction process using the generated discriminator for the excluded one subject, and accumulating errors between the diagnosis label and the result of prediction for the excluded one subject corresponds to execution of a so-called Leave-One-Out Cross Validation (LOOCV). Therefore, in the process shown in FIG. 12, by calculating the error mentioned above in each iteration, accumulating the errors and obtaining an average of L times, it is possible to perform the cross-validation of the generated discriminator or evaluate the generalization capability.

(Generation of Discriminator)

Again returning to FIG. 7, thereafter, data processing unit 32 generates the discriminator (S108) by the sparse logistic regression, based on the results of the outer loop feature selection (second sum-set).

Figure 14:
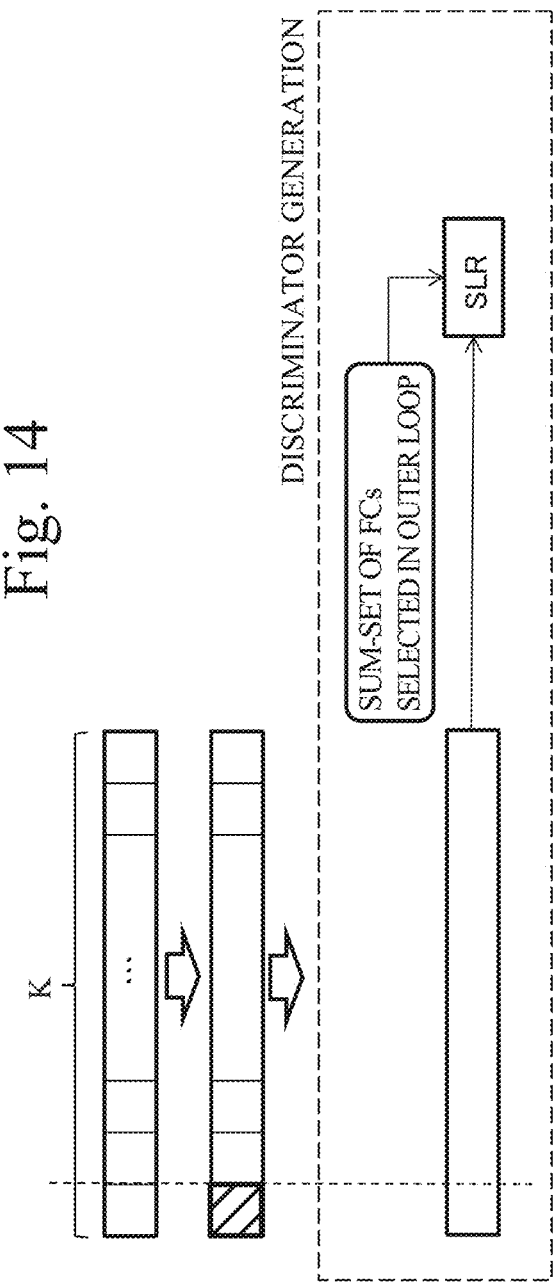
FIG. 14 shows a concept of the discriminator generation process at step S108.

FIG. 14 shows a concept of the discriminator generation process at step S108.

As shown in FIG. 14, at step S108, using the second sum-set extracted by the outer loop feature selection from the first sum-set as the explanatory variables, a discriminator is generated by sparse logistic regression on all subjects.

Discriminator data 3112 (data related to parameters and function form) for specifying the generated discriminator is stored in non-volatile storage device 2080, and later, when MRI measurement data (test data) different form the data used for the training described above is input, it is used to execute a discriminating process to estimate a diagnosis label for test data, Specifically, based on doctors' diagnosis in advance, the subjects are divided into a group of healthy individuals and a group of patients. Correlations (connections) of degrees of activities among brain regions (ROIs) of the subjects will be measured. By machine learning of measurement results, the discriminator is generated to discriminate whether the test data of a new subject different from those above, fits to disease or healthy. The discriminator thus functions as a biomarker of mental disorders.

Here, the "diagnosis label" as the biomarker output may include a probability that the subject has the disease (or probability that the subject is healthy), since the discriminator is generated by logistic regression. For example, an indication such as "probability that the subject has the disease is XX %" may be output. Such a probability may be used as a "diagnosis marker."

The attribute as the discriminator output is not limited to the discrimination of a disease, and the output may be related to other attributes. In that case also, the discriminator may output a discrete result that shows that attribute value belongs to which class, or may output a continuous value related to the attribute, for example, the probability of the attribute value belonging to a certain class.

In summary, in the biomarker learning (generation), in order to generate the biomarker for mental disorders, data of resting state functional connection MRI (rs-fcMRI) is used as an input, and the feature extraction is done by the above-described inner loop feature selection and outer loop feature selection, and then, by a discriminator generated by using the extracted features as explanatory variables, healthy/disease label discrimination is performed.

(Process in Inner Loop Feature Selection)

Figure 9:
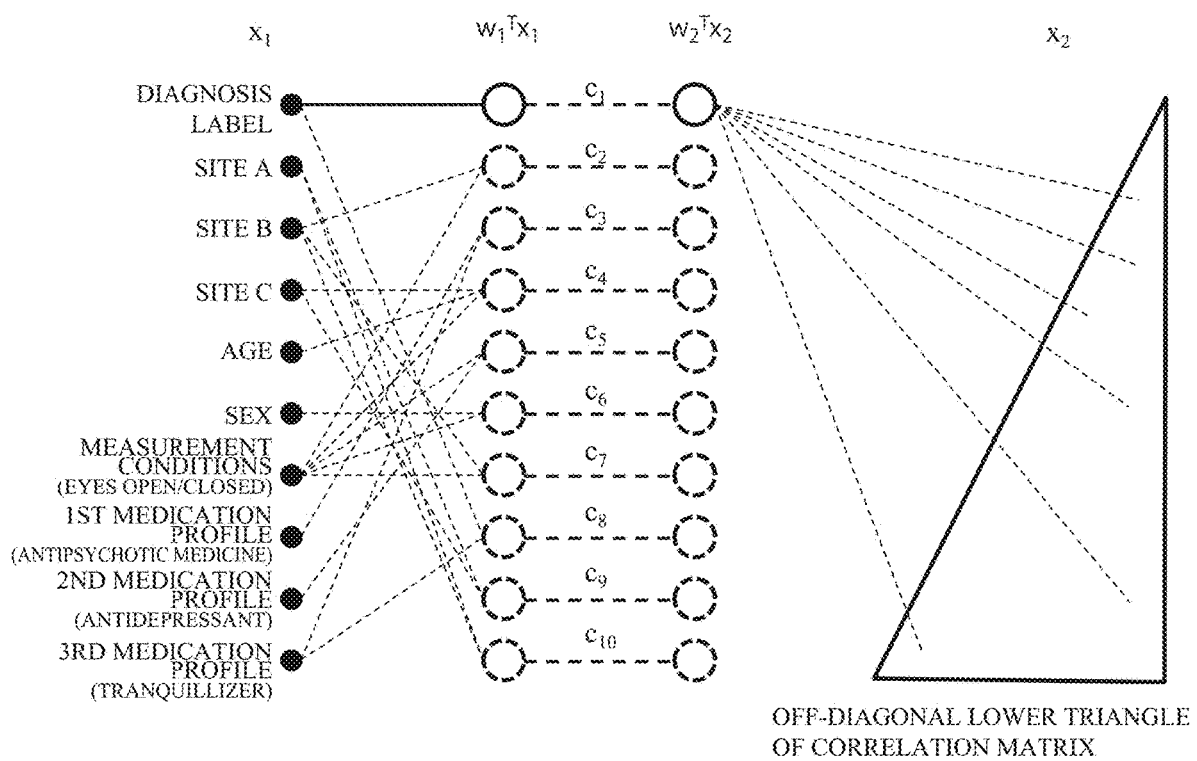
FIG. 9 illustrates the idea of an inner loop feature selecting process.

FIG. 9 illustrates the concept of the inner loop feature selecting process.

Figure 10:
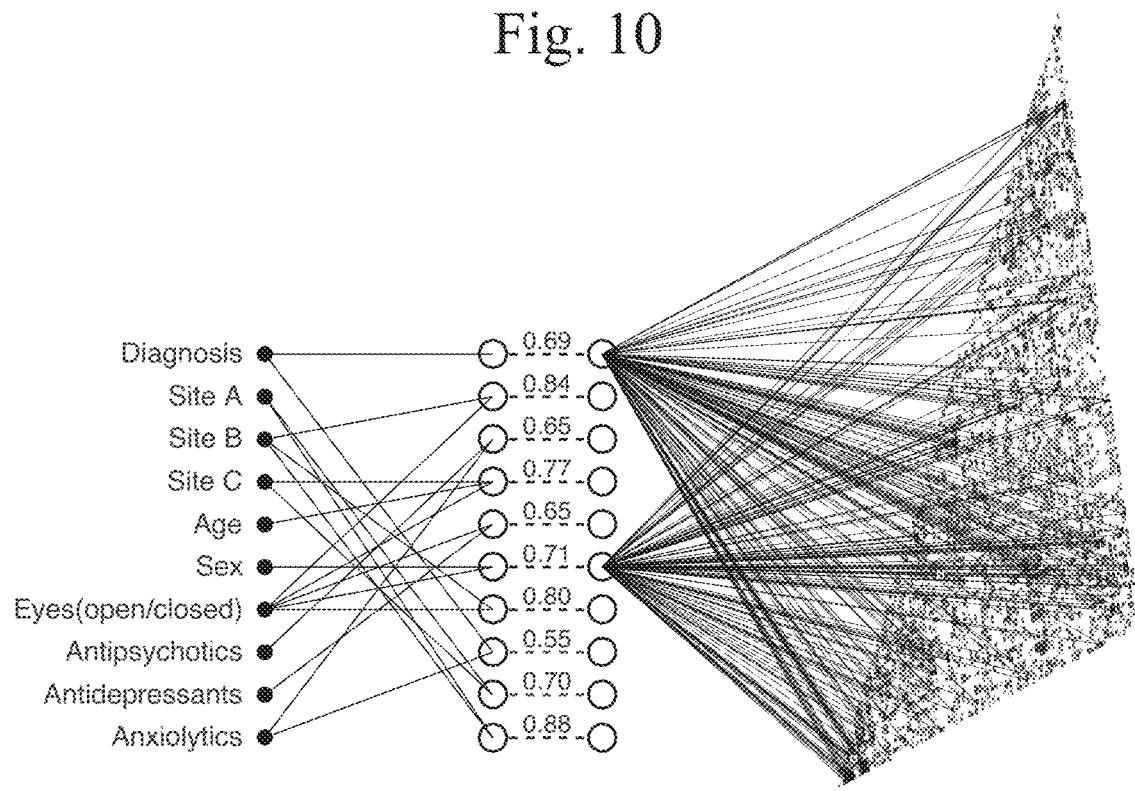
FIG. 10 shows, as an example, results on specific hyper parameters $\lambda_1$ and $\lambda_2$ among iteration processes performed at the time of the inner loop feature selection.

FIG. 10 shows, as an example, results on specific hyper parameters $X_1$ and $\lambda_2$ among the iteration processes performed at the time of the inner loop feature selection.

Referring to FIG. 9, here, one of the iterations of L1-SCCA of the nested feature selection is shown, where a canonical variable is connected only to the "diagnosis label."

In FIG. 9, that the canonical variable is connected only to the "diagnosis label" is represented by the diagnosis label connected by a solid line to only one canonical variable $w_1^T x_1$.

Further, the symbol $c_i$ on a dotted line connecting canonical variables $w_1^T x_1$ and $w_2^T x_2$ represents a correlation coefficient between respective canonical variables.

When the canonical variable $w_1^T x_1$ is connected only to the "diagnosis label," elements at the off-diagonal lower triangle of the correlation matrix representing the correlation of the functional connection connected to the corresponding canonical variable $w_2^T x_2$ are selected as features.

FIG. 10 shows, as an example, a combination of the smallest hyper parameters (here, $\lambda_1=0.4$, $\lambda_2=0.2$) that generates at least one canonical correlation for each piece of human attribute information among the first outer loop.

A canonical variable is represented by a circle.

Circles on the left column represent canonical variables $w_1^T x_1$ derived from the human characteristic information and the measurement conditions. On the other hand, circles on the right column represent canonical variables $w_2^T x_2$ derived from functional connections (FC).

As described above, the numerals on the dotted line connecting the canonical variables represent the correlation coefficients between the canonical variables $w_1^T x_1$ and $w_2^T x_2$.

Connections between labels of human attribute information and canonical variables $w_2^T x_2$ are represented by solid lines or dotted lines.

In this example, pay attention to an overlap between the first and sixth canonical variables respectively representing "diagnosis label," "sex" and "eyes open/closed condition."

The number of elements of the correlation matrix of the functional connections related to the first canonical variable was 745, that of the sixth canonical variable was 659, and the number of the overlapping elements of the correlation matrices of the functional connections was 141.

Further, the number of the elements of the correlation matrix of the functional connections selected by the outer loop feature selection overlapping the sixth canonical variable was only one.

Further, the combinations of lambdas which resulted in only one connection between the canonical variables and the "diagnosis" label occupied, in average, 17.6±5.0% of the overall combinations.

In average, the number of the elements of the correlation matrix of the functional connections related to the canonical variables of the "diagnosis" label was 925±798.

(Process in the Inner Loop Feature Selection)

Figure 11:
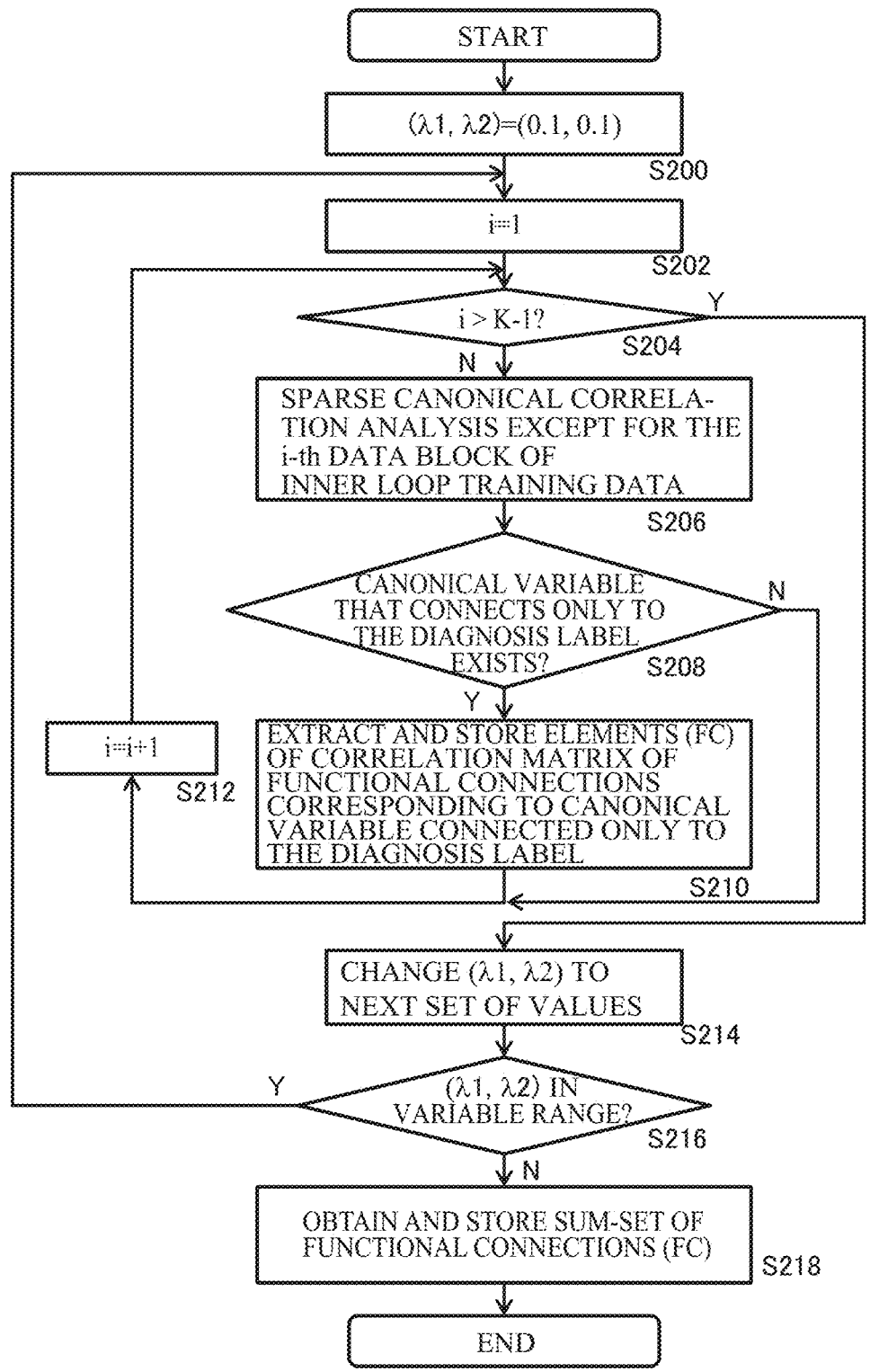
FIG. 11 is a flowchart showing in greater detail the process of the inner loop feature selection.

FIG. 11 is a flowchart showing in greater detail the process of the inner loop feature selection.

For the inner loop feature selection, the set of subjects are divided into K subsets as shown in FIG. 8(a), and of these, one subset is excluded and remaining (K-1) subsets are used.

Referring to FIG. 11, when the process of the inner loop feature selection starts, processor (CPU) 2040 sets hyper parameters $\lambda_1$ and $\lambda_2$ to initial values ($\lambda_1$, $\lambda_2$)=(0.1, 0.1) (S200).

Thereafter, the variable i is set to 1 (S202), and if the value i does not exceed the number of iteration (K-1) of the inner loop feature selection (N at S204), CPU 2040 executes the sparse canonical correlation analysis (S206) based on the subjects' human attribute information 3104 and on functional connection correlation matrix data 3106 stored in non-volatile storage device 2080, except for the i-th data block of the inner loop training data.

If there exists canonical variables that connect only to the diagnosis label for the present set of ($\lambda_1$, $\lambda_2$) (Y at S208), CPU 2040 extracts elements (FC) of the correlation matrix of the functional connections corresponding to the canonical variable that connects only to the diagnosis label, and stores them in non-volatile storage device 2080 (S210). Following the process at step S210, or if there is no canonical variable that connects only to the diagnosis label for the present set of ($\lambda_1$, $\lambda_2$) (N at S208), the value i is incremented by 1 and the process returns to step S204.

Therefore, CPU 2040 repeats the process of steps S206 to S212 for (K-1) times.

At step S204, if the value i exceeds the number of iteration (K-1) of the inner loop feature selection (Y at S204), CPU 2040 changes either one of $X_1$ and $\lambda_2$ of ($\lambda_1$, $\lambda_2$) by a prescribed step amount in accordance with a prescribed rule (S214). At step S216, if the value of ($\lambda_1$, $\lambda_2$) is in the variable range (Y at S216), CPU 2040 returns the process to step S202.

When the process completes for all sets of possible values of ($\lambda_1$i, $\lambda_2$) (N at S216), CPU 2040 obtains a sum-set of elements (FC) of the correlation matrix of the functional connections extracted by the processes so far, and stores them as first functional connection sum-set data 3108 in non-volatile storage device 2080, and thus, the process ends.

(Process in Outer Loop Feature Selection)

Figure 13:
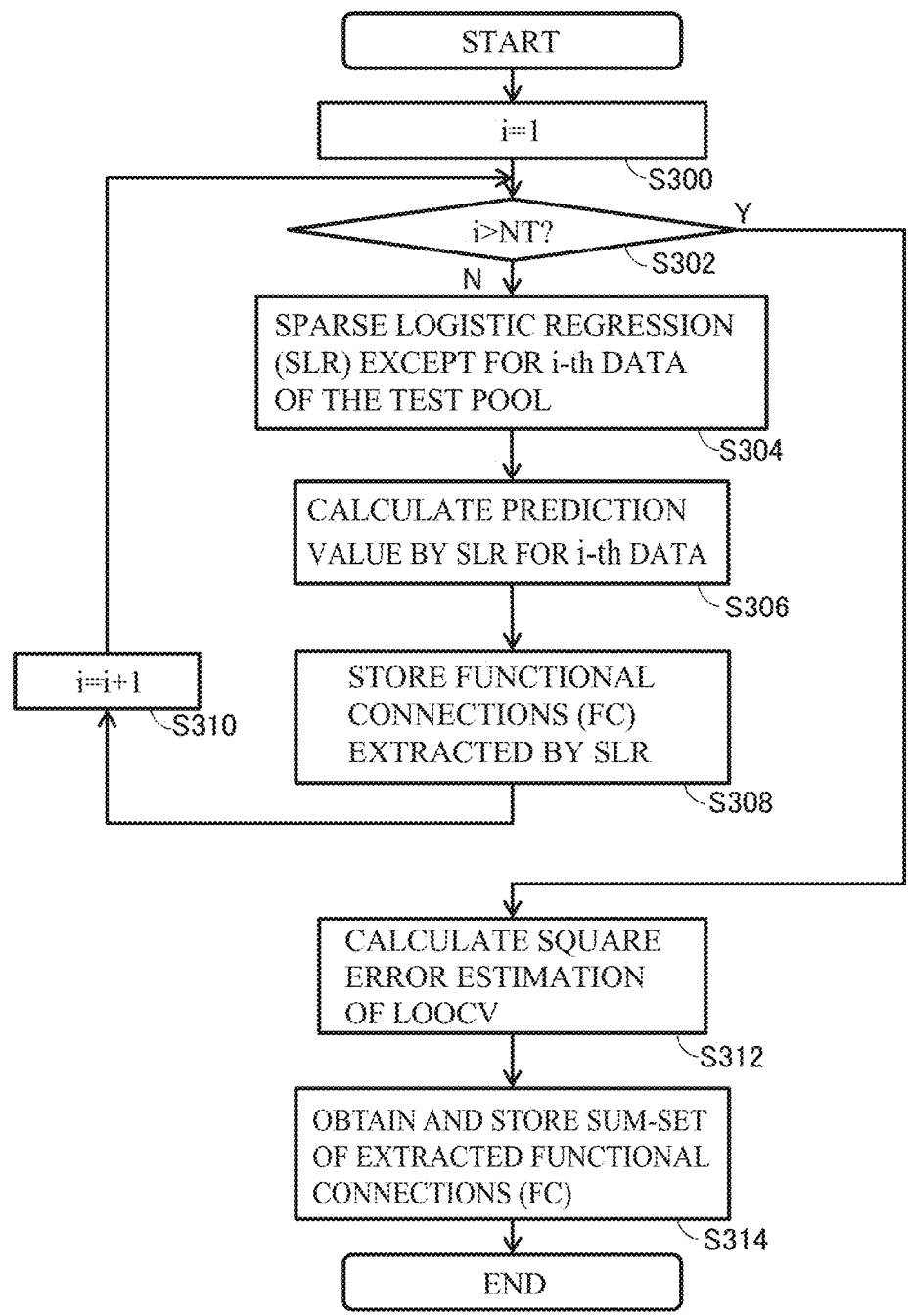
FIG. 13 is a flowchart showing in greater detail the process of the outer loop feature selection.

FIG. 13 is a flowchart showing in greater detail the process of the outer loop feature selection.

In the outer loop feature selection, the set of subjects are divided into K subsets as shown in FIG. 12, and of these, one subset not used in the inner loop feature selection is used as a test pool. The number of subjects included in the test pool is given as NT.

Further, in the following example, Leave-One-Out Cross Validation (LOOCV) will be performed.

Referring to FIG. 13, when the process of the outer loop feature selection starts, processor (CPU) 2040 sets the variable i to 1 (S300), and if the value i does not exceed the number of iteration NT of the outer loop feature selection (N at S302), CPU 2040 executes the sparse logistic regression (SLR) based on the subjects' human attribute information 3104 and on the functional connection correlation matrix data 3106 stored in non-volatile storage device 2080, except for the i-th data of the test pool, and thereby generates a test discriminator (S304).

Thereafter, using the generated test discriminator, CPU 2040 calculates a prediction value by SLR for the excluded i-th data (S306).

Further, CPU 2040 stores the functional connection FC extracted by the operation of sparring at the time of generating the test discriminator as the selected features in non-volatile storage device 2080, and increments the value i by one (1) (S310).

When the process of S304 to S308 is repeated NT times and the variable i exceeds NT (Y at S302), CPU 2040 estimates the square error of LOOCV (S312).

Thereafter, by the iteration of NT times, CPU 2040 obtains a sum-set (second sum-set) of the extracted functional connections FC and stores it as the second functional connection sum-set data 3110 in non-volatile storage device 2080, and the process ends.

(Discriminator Generation Process)

FIG. 14 shows a concept of eventual discriminator generation process.

As shown in FIG. 14, in the discriminator generation process, second functional connection sum-set data 3110 eventually extracted by the inner loop feature selection process and the outer loop feature selection process is used as the explanatory variables, and the discriminator is generated by the sparse logistic regression for every subject.

(Eventually Extracted Elements of Correlation Matrix of Functional Connectivity)

Figure 15:
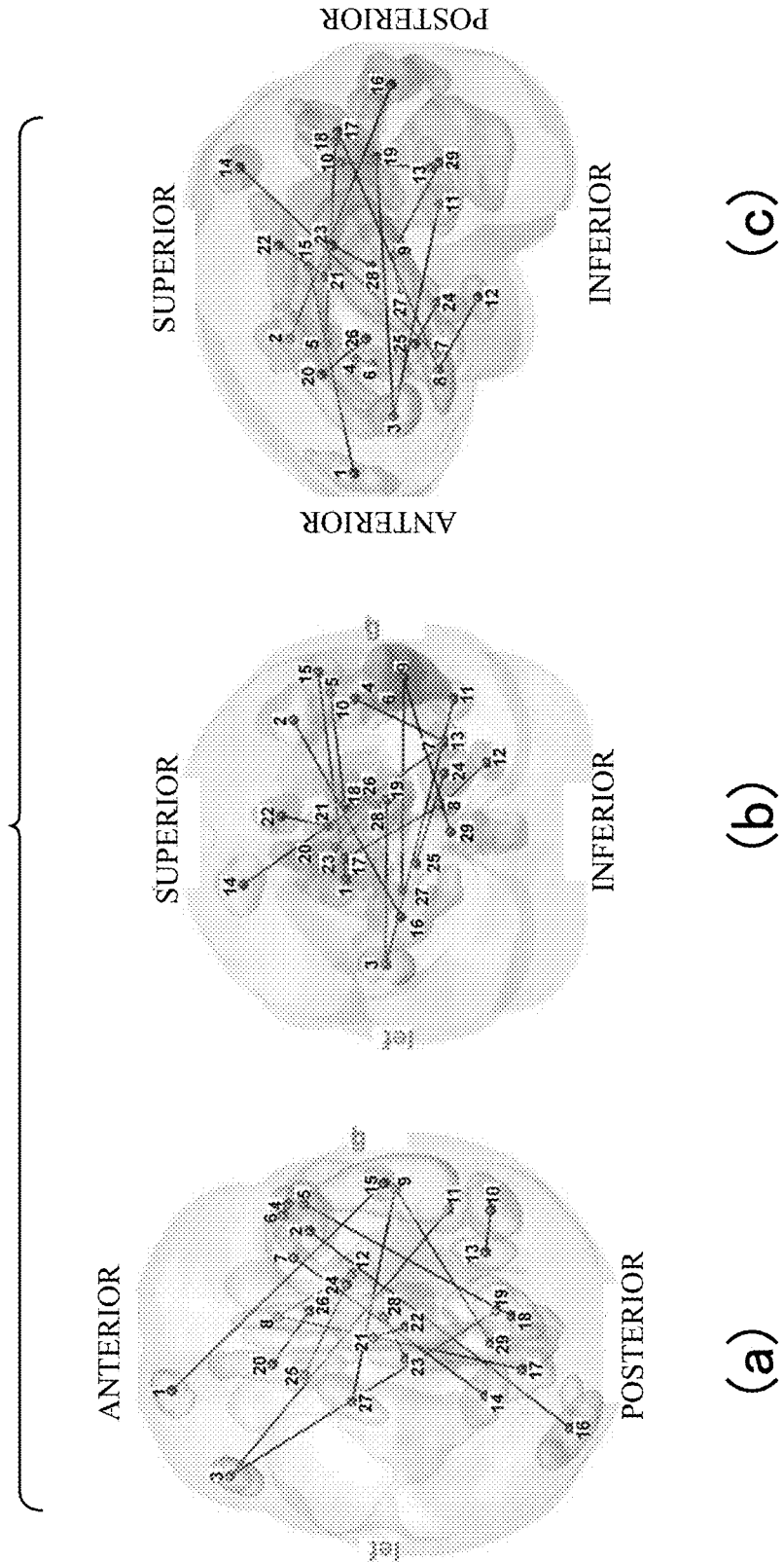
FIG. 15 shows elements of a correlation matrix of eventually selected functional connections among 181 Japanese subjects (74 ASD patients and 107 neurotypicals).

FIG. 15 shows elements of correlation matrix of eventually selected functional connections among 181 Japanese subjects (74 ASD patients and 107 neurotypicals).

In the example described above, for an ASD/TD discriminator, sixteen (16) elements (FC) of the correlation matrix of the functional connections were selected.

FIG. 15(a) is a view from the top of the head (parietal region), FIG. 15(b) is from the back of the head (occipital region), and FIG. 15(c) is from the left side of the head (left temporal region).

Figure 16:
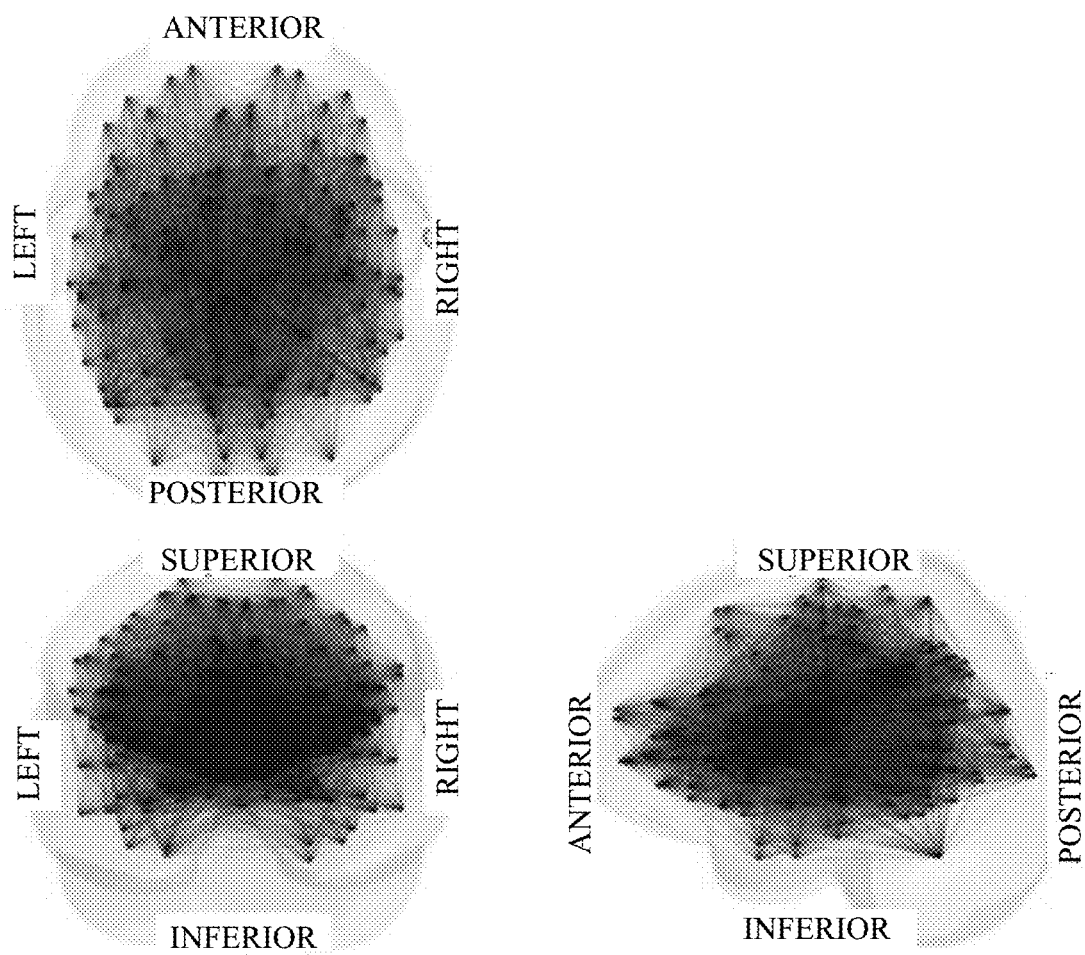
FIG. 16 shows all 9730 elements of the correlation matrix of functional connections (FC) respectively viewed from sides corresponding to FIG. 15.

Further, FIG. 16 shows all 9730 elements of the correlation matrix of the functional connections (FC) respectively viewed from sides corresponding to FIG. 15.

In FIG. 15, to twenty-nine (29) terminal regions connected by sixteen (16) FC, the following numbers are allotted.

In frontal cortex, superior frontal gyrus (1), middle frontal gyrus (2) and inferior frontal gyrus (3 left and; 4-7 right), and straight gyrus (8);

in temporal lobe, superior temporal gyrus (9), middle temporal gyrus (10), inferior temporal gyrus (11), parahippocampal gyrus (12) and fusiform gyrus (13);

in parietal lobe, superior parietal lobule (14) and posterior central gyrus (15); in occipital lobe, middle occipital gyrus (16), cuneus of the occipital lobe (17 left; 18 right) and calcarine fissure (19);

in cerebral limbic system, anterior cingulated gyrus (20), middle cingulated gyrus (21-22), posterior cingulated gyrus (23) and amygdale (24);

in basal ganglia, caudate nuculai (25 left; 26 right), pale globe (27), thalamus (28); and cerebellum (29).

(Importance of the Final sixteen (16) FC Selected in LOOCV)

In an example described with reference to autism, the sixteen (16) functional connections FC finally incorporated in the discriminator were selected by the sparse logistic regression using a data set of 181 Japanese, using sub-sets of FC reduced by the inner loop and the outer loop feature selections as explanatory variables.

In the following, whether the finally selected sixteen (16) functional connections FC have been frequently selected with a heavy weight in the overall outer loop procedure or not will be discussed. This is important considering the stability and robustness of the finally selected sixteen (16) functional connections FC.

For this purpose, an accumulative absolute weight for k-th FC (k=1, 2, ..., 9730) is defined by Equation (4) below.

$$c^k = \sum_{i=1}^{N} |w_i^k| \qquad (4)$$

Here, N=181 is the number of LOOCV (that is, the number of subjects), and $w_i^k$ represents a weight related to the k-th functional connection FC of i-th LOOCV.

The heavier accumulative weight $c_i^k$ means that the k-th functional connection FC makes more important contributions to the classification of ASD and TD, over the entire LOOCV.

Figure 17:
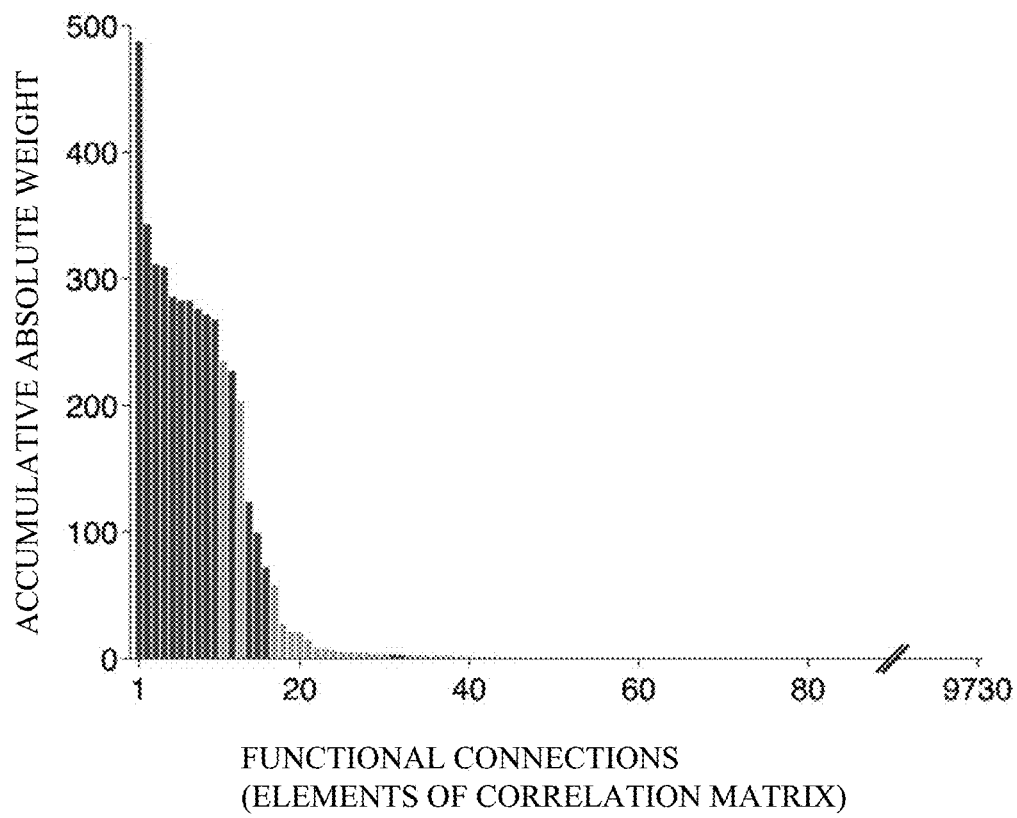
FIG. 17 shows a distribution of magnitude of 48 non-zero $c_i^k$.

FIG. 17 shows a distribution of the magnitudes of the forty-eight (48) non-zero $c_i^k$.

When sorted by magnitude, it can be seen that the selected sixteen (16) functional connections FC (black) represent an important subset among the forty-eight (48) functional connections FC (gray) that are at least once selected in LOOCV.

Therefore, we can conclude that the finally selected sixteen (16) FC are stable and robust and therefore reliable, with respect to the subsets of LOOCV of the 181 subjects.

The heavier accumulative absolute weight means greater contributions by the functional connections to the discriminator.

(Biomarker Verification)

Figure 18:
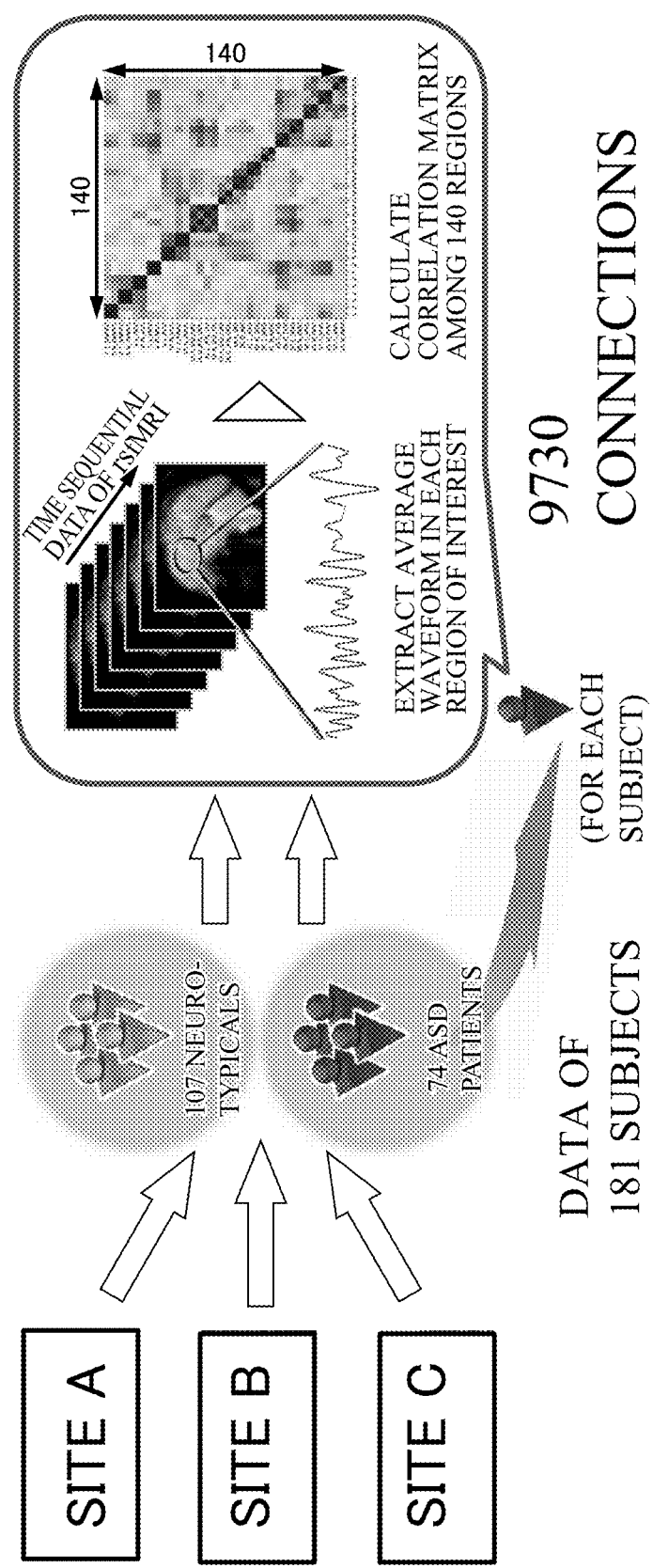
FIG. 18 illustrates a procedure for verifying a generated biomarker.

FIG. 18 illustrates a procedure for verifying the biomarker generated in the above-described manner.

Using the parameters for discrimination and functional connections FC extracted by learning based on the data of 107 subjects of TD group and 74 subjects of ASD patients group collected at sites A to C in Japan, disease/healthy labels were predicted for the data not used for the parameter learning, and consistency with the actual disease discriminating label was evaluated.

FIG. 19 shows attribute data of subjects at sites A to C.

At sites A and B, both the TD group and the ASD group were subjected to measurement, while at site C, only the TD group was measured.

Here, the "dominant hand" is indicated by an index. Such index is disclosed, for example, in the reference below.

Oldfield, R. C. (1971). The assessment and analysis of handedness: the Edinburgh inventory. Neuropsychologia 9, 97-113.

This is the data to see the relation between the dominant hand or dominance of left/right brain with ASD.

IQ represents intelligence quotient.

Figure 20:
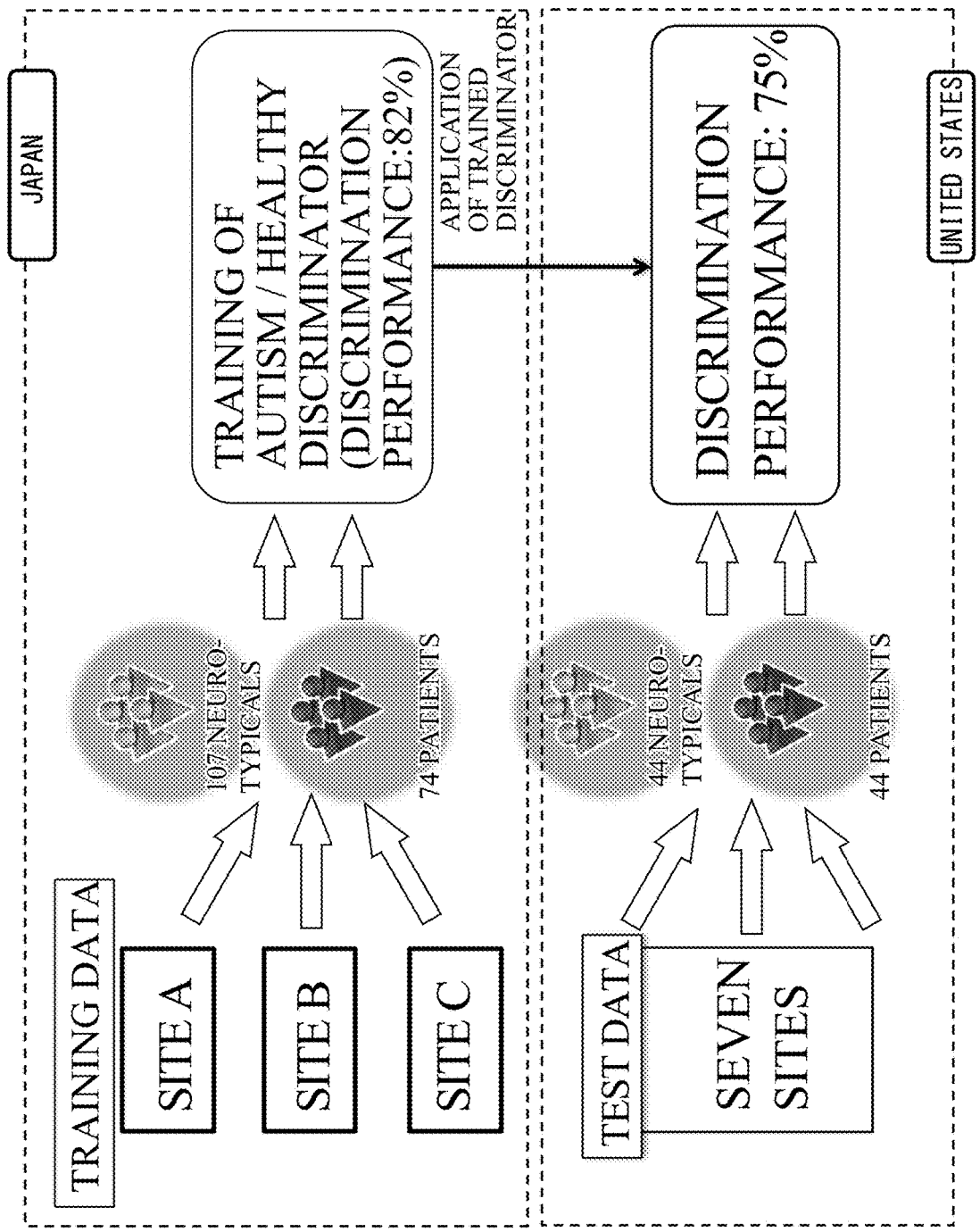
FIG. 20 shows the generalization performance of the biomarker.

FIG. 20 shows generalization performance of the biomarker described above.

When the biomarker was generated by the method as described above, the discrimination performance was 82% for the data of three different sites in Japan. When rs-fcMRI data measured at seven (7) sites in the United States were used as inputs for the biomarker using the same parameters, the discrimination performance was at least 75%.

In FIG. 20, generalization to the United States indicates excellence of performance of the biomarker obtained by learning with limited subject data, considering different criteria for diagnosis over race and nation.

FIG. 21 shows the attributes of those subjects in the United States.

In this figure, site IDs are as follows:
CAL: California Institute of Technology
CMA: Carnegie Mellon University
NYU: New York University
OLN: Institute of Living at Hartford Hospital
PIT: University of Pittsburgh, Medical Center
TTY: Trinity Centre for Health Sciences
USM: The University of Utah, School of Medicine (Multi-disease Biomarker)

In the foregoing, regarding criterion variable of SCCA, the diagnosis label is related to one disease.

When the rs-fcMRI data is used as explanatory variables, if a plurality of disease labels are to be used as disease labels, application as a multi-disease marker is possible.

Here, the disease labels may include a label for discriminating disease/healthy for each of the plurality of diseases.

The diagnosis label mentioned above may include diagnosis labels of "autism," "schizophrenia," "depression," "obsessive-compulsive disorders," and the like.

While such diagnosis labels are only fictitious examples, by studying relations between brain activities and diseases that have been called by different names, or influence of medicines administered to respective diseases, using the (SCCA+SLR) method on the rs-fcMRI data, it is possible to extract respective correlations.

Medication profile labels may include type of medicines such as "first psychotropic drug" and "second psychotropic drug" as well as pieces of information related to the dose, period of administration and the like of each medicine.

The measuring conditions may include the information related to the performance of fMRI imaging device such as described above (for example, the intensity of applied magnetic field), and the information as to whether the eyes were open or closed during measurements.

Further, the characteristic information of subjects may include the information of age, sex, and the like.

Second Embodiment

In the configuration described in the first embodiment, the brain activity measuring device (fMRI device) measures data of brain activities obtained at a plurality of measuring sites and based on the brain activity data, generation of biomarkers and estimation (prediction) of diagnosis labels by the biomarkers are realized by processing by one computer or by distributed processing.

It is noted, however, that i) measurement of brain activity data for training a biomarker through machine learning (data collection), ii) the process of generating a biomarker through machine learning and the process of estimating (predicting) diagnosis labels by the biomarker for a specific subject (estimation process), and iii) measurement of brain activity data of the specific subject above (measurement of subject's brain activities), may be executed in a distributed manner at different sites.

Figure 22:
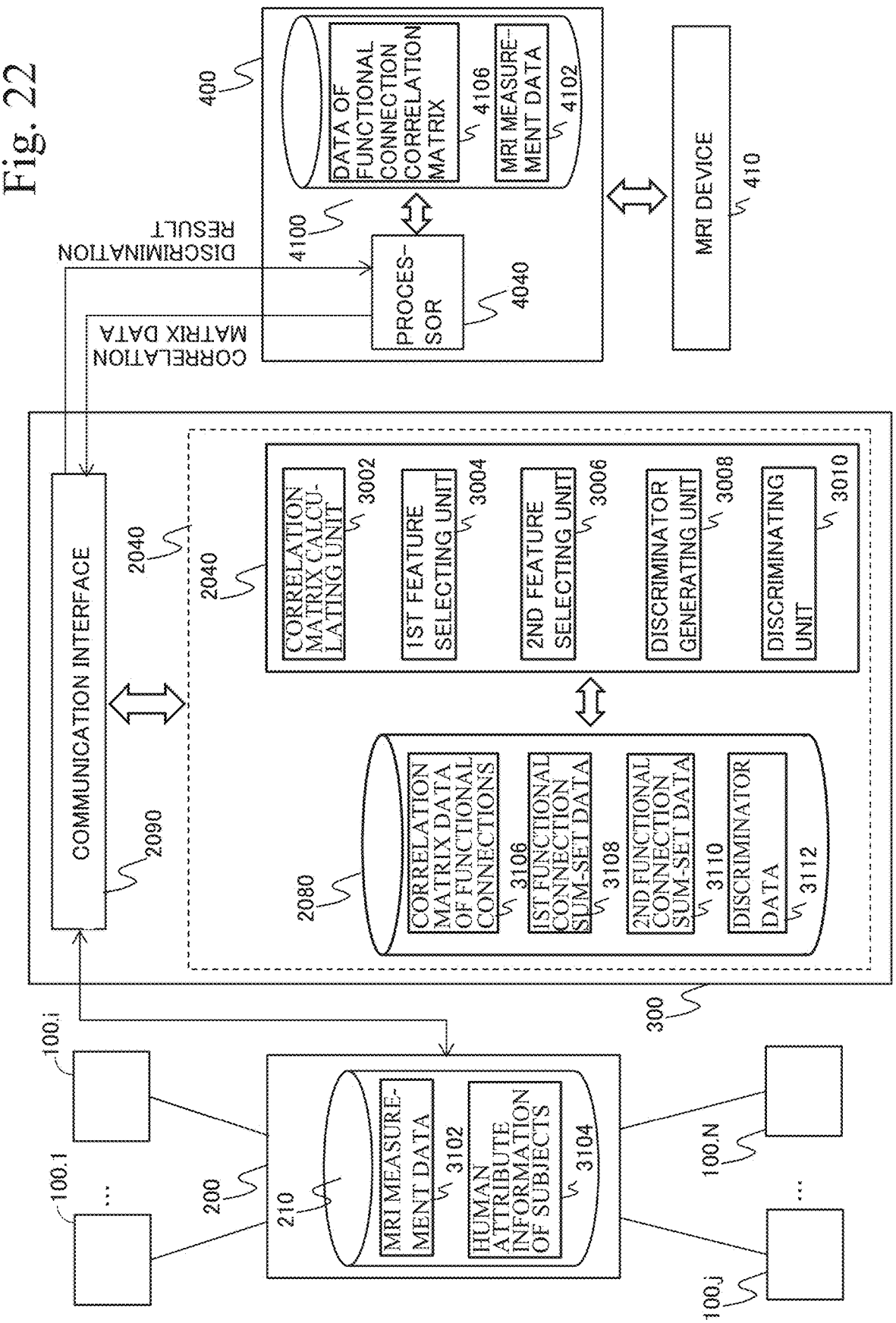
FIG. 22 is a functional block diagram showing an example when data collection, an estimating process and the measurement of brain activities of subjects are processed in a distributed manner.

FIG. 22 is a functional block diagram showing an example when data collection, the estimating process and the measurement of brain activities of subjects are processed in a distributed manner.

Referring to FIG. 22, sites 100.1 to 100.N represent sites at which data of healthy group and patient group are measured by brain activity measuring devices, and a management server 200 manages measurement data from sites 100.1. to 100.N.

A computer 300 generates a discriminator from the data stored in server 200.

An MRI device 410 is provided at a separate site that utilizes the results from the discriminator on computer 300, and measures data of the brain activities of a specific subject.

A computer 400 is provided on a separate site where MRI device 410 is installed, and calculates the correlation data of the brain functional connection of the specific subject from the measurement data of MRI device 410, sends the correlation data of functional connection to computer 300, and utilizes the results from the discriminator that are sent back.

Server 200 stores the MRI measurement data 3102 of patient group and healthy group transmitted from sites 100.1 to 100.N as well as the human attribute information 3104 of the subject associated with the MRI measurement data 3102, and in accordance with an access from computer 300, transmits these data to computer 300.

Computer 300 receives MRI measurement data 3102 and human attribute information 3104 of the subject from server 200 through a communication interface 2090.

Hardware configurations of server 200, computer 300 and computer 400 are basically the same as the configuration of "data processing unit 32" described with reference to FIG. 2 and, therefore, description thereof will not be repeated here.

Returning to FIG. 22, a correlation matrix calculating unit 3002, a first feature selecting unit 3004, a second feature selecting unit 3006, a discriminator generating unit 3008 and discriminating unit 3010, as well as correlation matrix data 3106 of functional connection, first functional connection sum-set data 3108, second functional connection sum-set data 3110 and discriminator data 3112 are the same as those described in the first embodiment and, therefore, description thereof will not be repeated here.

MRI device 410 measures the brain activity data of a subject whose diagnosis label is to be estimated, while processor 4040 of computer 400 stores the measured MRI measurement data 4102 in a non-volatile storage device 4100.

Further, a processor 4040 of computer 400 calculates functional connection correlation matrix data 4106 in the similar manner as correlation matrix calculating unit 3002, based on MRI measurement data 4102 and human attribute information of subjects of measurements by MRI device 410, and stores the calculated data in non-volatile storage device 4100.

A disease as an object of diagnosis is designated by a user of computer 400 and in accordance with an instruction of transmission by the user, computer 400 transmits the functional connection correlation matrix data 4106 to computer 300. In response, discriminating unit 3010 calculates the result of discrimination on the designated diagnosis label, and computer 300 transmits it to computer 400 through communication interface 2090.

Computer 400 informs the user of the result of discrimination using a display device or the like, not shown.

By such a configuration, it is possible to provide a larger number of users with the result of estimation of diagnosis label by the discriminator, based on the data collected from a larger number of users.

Further, server 200 and computer 300 may be managed by separate administrators. In that case, by limiting the computers that can access to server 200, it becomes possible to improve the security of subject information stored in server 200.

Further, from the viewpoint of the operator of computer 300, the "service of providing result of discrimination" becomes possible while not providing, any information at all of the discriminator to the "side (computer 400) receiving the service of discrimination by the discriminator."

In the descriptions of 1st and 2nd Embodiments above, it is assumed that real-time time fMRI is used as the brain activity detecting apparatus for time-sequentially measuring brain activities by functional brain imaging. It is noted, however, that any of the fMRI described above, a magnetoencephalography, a near-infrared spectroscopy (NIRS), an electroencephalography or any combination of these may be used as the brain activity detecting apparatus. Regarding such a combination, it is noted that fMRI and NIRS detect signals related to change in blood stream in the brain, and have a high spatial resolution. On the other hand, magnetoencephalography and electroencephalography are characterized in that they have a high temporal resolution, for detecting changes in an electromagnetic field associated with the brain activities. Therefore, if fMRI and the magnetoencephalography are combined, brain activities can be measured with both spatially and temporally high resolutions. Alternatively, by combining NIRS and the electroencephalography, a system for measuring the brain activities with both spatially and temporally high resolutions can also be implemented in a small, portable size.

By the configurations above, a brain activity analyzing apparatus and a brain activity analyzing method functioning as a biomarker using brain function imaging for neurological/mental disorders can be realized.

In the foregoing, an example has been described in which a "diagnosis label" is included as an attribute of a subject, and by generating a discriminator through machine learning, the discriminator is caused to function as a biomarker. The present invention, however, is not necessarily limited to such an example. Provided that a group of subjects whose results of measurements are to be obtained as the object of machine learning is classified into a plurality of classes in advance by an objective method, the correlation of degrees of activities (connection) among brain regions (ROIs) of the subjects are measured and a discriminator can be generated for classification by machine learning using the measured results, the present invention may be used for other discrimination.

Further, as mentioned above, such discrimination may indicate by probability whether it belongs to a certain attribute.

Therefore, it is possible to objectively evaluate whether taking a certain "training" or following a certain "behavior pattern" is effective to improve the health of a subject or not. Further, it is also possible to objectively evaluate whether certain ingestions of "food" or "drink" or a certain activity or activities are effective to reach a healthier state before onset of a disease (in the state of "not yet diseased").

Further, even before the onset of a disease, if an indication such as "probability of being healthy: XX %" is output as mentioned above, it is possible to provide the user with an objective numerical value of his/her state of health. Here, the output may not necessarily be the probability. For example, "a continuous value of degree of healthiness, such as probability of being healthy" converted to a score may be displayed. By providing such a display, the apparatus in accordance with the embodiments of the present invention can be used as an apparatus for health management of users.

In the example of FIG. 22, it has been described that the functional connection correlation matrix data 4106 only is transmitted from computer 400 to computer 300.

The configuration, however, is not necessarily limited to the above. For example, MRI measurement data 4102 and subjects' human attribute data in anonymized form may be transmitted from computer 400 to computer 300. Then, in computer 300, functional connection correlation matrix data 3106 is calculated, based on this, discriminating unit 3010 calculates the result of discrimination for the designated diagnosis label, and computer 300 may transmit the result of discrimination to computer 400 through communication interface 2090.

Here, the MRI measurement data 4102 and the subjects' human attribute data transmitted in the anonymized state from computer 400 may be transferred from computer 300 to server 200 and may be stored in server 200. It is also possible in computer 300 to execute machine learning based on the data in server 200 accumulated in this manner and to update the discriminator of discriminating unit 3010.

By such a configuration also, it is possible to provide the result of estimation of diagnosis label by the discriminator to a larger number of users based on the data collected from a larger number of subjects.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

INDUSTRIAL APPLICABILITY

As described above, the present invention is applicable to apparatuses for obtaining data to enable objective determination of healthy or disease condition with respect to the states of the brain activities. Further, it can also be applicable to a biomarker apparatus based on the brain function imaging related to neurological/mental disorders.

REFERENCE SIGNS LIST

2 subject, 6 display, 10 MRI apparatus, 11 magnetic field applying mechanism, 12 static magnetic field generating coil, 14 magnetic field gradient generating coil, 16 RF irradiating unit, 18 bed, 20 receiving coil, 21 driving unit, 22 static magnetic field power source, 24 magnetic field gradient power source, 26 signal transmitting unit, 28 signal receiving unit, 30 bed driving unit, 32 data processing unit, 34 display control unit, 36 storage unit, 38 display unit, 40 input unit, 42 control unit, 44 interface unit, 46 data collecting unit, 48 image processing unit, 50 network interface.

The invention claimed is:
1. A brain activity analyzing apparatus, comprising:
a memory storing data representing signals obtained by a brain activity detecting device for time-sequentially measuring in advance signals representing brain activities at a plurality of prescribed regions in a brain of each of a plurality of subjects, a plurality of attribute information items being associated with each of the plurality of subjects; and
one or more processors configured to:
i) calculate, for each of the subjects, a correlation matrix of brain activities among the plurality of prescribed regions from the measured signals, ii) extract elements of the correlation matrix that connect to a canonical variable corresponding only to a specific attribute information item among the plurality of attribute information items by successively selecting, from M (M: natural number not smaller than 2) different subsets extracted from the plurality of subjects, one subset and by performing a sparse canonical correlation analysis on the plurality of attribute information items and on elements of the correlation matrix of (M-1) subsets except for the selected one subset, iii) obtain, for the successively selected subsets, a first sum-set as a sum-set of elements of the extracted correlation matrix, and iv) generate a discriminator for estimating the specific attribute information item from the elements of the first sum-set;

v) store information for specifying the calculated discriminator to a storage device; and vi) perform a process of discriminating input data based on the discriminator specified by the information stored in the storage device.

2. The brain activity analyzing apparatus according to claim 1, wherein
said one or more processors calculate the discriminator for estimating the specific attribute information item from the first sum-set by sparse logistic regression.

3. The brain activity analyzing apparatus according to claim 1, wherein
when subjects other than the above-described M subsets of the plurality of subjects are used as a test set and the test set is divided into N (N: natural number not smaller than 2) different groups,
said one or more processors are further configured to:
perform feature extraction to calculate, by sparse logistic regression, a test discriminator for estimating the specific attribute information item based on the first sum-set, on a set of subjects except for one group selected from the N groups of the plurality of subjects, and for extracting elements of the correlation matrix that become the explanatory variables of the test discriminator in the process of sparring, and
iterate the feature extraction while successively selecting one group from the N groups for obtaining a second sum-set as the sum-set of elements of the correlation matrix extracted as the explanatory variables of test discriminator; and
calculate the discriminator for estimating the specific attribute information item from the second sum-set by sparse logistic regression.

4. The brain activity analyzing apparatus according to claim 3, wherein
said one or more processors are further configured to perform cross-validation by calculating a result of discrimination by the test discriminator calculated by the feature extraction while successively selecting one group to be excluded from the N groups, using the excluded group as a test sample.

5. The brain activity analyzing apparatus according to claim 1, wherein the specific attribute information item is a diagnosis label of a subject.

6. A non-transitory computer readable medium having stored thereon instructions that cause a computer having a processing device and a storage device to execute a brain activity analysis based on information from a brain activity detecting device for measuring brain activities of a plurality of subjects; wherein a plurality of attribute information items are associated with each of the plurality of subjects;
the instructions cause the computer to execute a step of the processing device generating a discriminator, from information obtained by the brain activity detecting device time-sequentially measuring in advance brain activities at a plurality of prescribed regions in a brain of each of a plurality of subjects;
the step of generating a discriminator includes the steps of:
i) calculating, for each of the subjects, a correlation matrix of brain activities among the plurality of prescribed regions from the measured signals,
ii) extracting elements of the correlation matrix that connect to a canonical variable corresponding only to a specific attribute information item among the plurality of attribute information items by successively selecting, from M (M: natural number not smaller than 2) different subsets extracted from the plurality of subjects, one subset and by performing a sparse canonical correlation analysis on the attribute information items and on elements of the correlation matrix of (M-1) subsets except for the selected one subset,
iii) obtaining, for the successively selected subsets, a first sum-set as a sum-set of elements of the extracted correlation matrix, and
iv) calculating a discriminator for estimating the specific attribute information item from the elements of the first sum-set;
the program further causes the computer to execute the steps of:
storing information for specifying the calculated discriminator in the storage device; and
performing a process of discriminating input data based on the discriminator specified by the information stored in the storage device.

7. The non-transitory computer readable medium according to claim 6, wherein the step of calculating a discriminator includes the step of calculating the discriminator for estimating the specific attribute information item from the first sum-set by sparse logistic regression.

8. The non-transitory computer readable medium according to claim 6, wherein the step of generating a discriminator includes the steps of:
when subjects other than the above-described M subsets of the plurality of subjects are used as a test set and the test set is divided into N (N: natural number not smaller than 2) different groups,
calculating, by sparse logistic regression, a test discriminator for estimating the specific attribute information item based on the first sum-set, on a set of subjects except for one group selected from the N groups of the plurality of subjects, and extracting elements of the correlation matrix that become the explanatory variables of the test discriminator in the process of the sparsing, and
iterating feature extraction at the step of extracting elements while successively selecting one group from N groups and thereby obtaining a second sum-set as the sum-set of elements of the correlation matrix extracted as the explanatory variables of the test discriminator; and wherein
at the step of calculating a discriminator, the discriminator for estimating the specific attribute information item from the second sum-set is calculated by sparse logistic regression.

9. The non-transitory computer readable medium according to claim 8, wherein the step of generating a discriminator further includes the step of:

performing cross-validation by calculating a result of discrimination by the test discriminator calculated at the step of extracting elements while successively selecting one group to be excluded from the N groups, using the excluded group as a test sample.

10. The non-transitory computer readable medium according to claim 6, wherein the specific attribute information item is a diagnosis label of a subject.

11. A brain activity analyzing apparatus, comprising:
a memory storing data representing signals obtained by a brain activity detecting device time-sequentially measuring in advance signals representing brain activities at a plurality of prescribed regions in a brain of each of a plurality of subjects, wherein a plurality of attribute information items are associated with each of the plurality of subjects;
one or more processors configured to generate a discriminator that estimates a specific attribute information item of a subject;
a storage device connected to the one or more processors for storing information that specifies the discriminator generated by the one or more processors; and
a discriminating device for performing a process of discriminating input data based on the discriminator specified by the information stored in the storage device; wherein
the one or more processors are programmed to
i) calculate, for each of the subjects, a correlation matrix of brain activities among the plurality of prescribed regions from the measured signals,
ii) extract elements of the correlation matrix that connect to a canonical variable corresponding only to a specific attribute information item among the plurality of attribute information items by successively selecting, from M (M: natural number not smaller than 2) different subsets extracted from the plurality of subjects, one subset and by performing a sparse canonical correlation analysis on the attribute information items and on elements of the correlation matrix of (M-1) subsets except for the selected one subset,
iii) obtain, for the successively selected subsets, a first sum-set as a sum-set of elements of the extracted correlation matrix, and
iv) calculate a discriminator for estimating the specific attribute information item from the elements of the first sum-set.

12. A brain activity analyzing method causing a computer having a processing device and a storage device to execute a brain activity analysis based on information from a brain activity detecting device for measuring brain activities of a plurality of subjects; wherein
a plurality of attribute information items are associated with each of the plurality of subjects;
the method comprising a step of the processing device generating a discriminator, from information obtained by the brain activity detecting device time-sequentially measuring in advance brain activities at a plurality of prescribed regions in a brain of each of the plurality of subjects;
the step of generating a discriminator includes the steps of:
i) calculating, for each of the subjects, a correlation matrix of brain activities among the plurality of prescribed regions from the measured signals,
ii) extracting elements of the correlation matrix that connect to a canonical variable corresponding only to a specific attribute information item among the plurality of attribute information items by successively selecting, from M (M: natural number not smaller than 2) different subsets extracted from the plurality of subjects, one subset and by performing a sparse canonical correlation analysis on the attribute information items and on elements of the correlation matrix of (M-1) subsets except for the selected one subset,
iii) obtaining, for the successively selected subsets, a first sum-set as a sum-set of elements of the extracted correlation matrix, and
iv) calculating a discriminator for estimating the specific attribute information item from the elements of the first sum-set;
the method further comprising the steps of:
storing information for specifying the calculated discriminator in the storage device; and
performing a process of discriminating input data based on the discriminator specified by the information stored in the storage device.

13. A biomarker apparatus, comprising:
a storage device storing information for specifying a discriminator generated by one or more first processors from signals obtained by a brain activity detecting device time-sequentially measuring in advance signals representing brain activities at a plurality of prescribed regions in a brain of each of a plurality of subjects; and
one or more second processors configured to perform a process of discriminating input data based on the discriminator specified by the information stored in the storage device; wherein
a plurality of attribute information items are associated with each of the plurality of subjects;
the one or more first processors are configured to:
i) calculate, for each of the subjects, a correlation matrix of brain activities among the plurality of prescribed regions from the measured signals,
ii) extract elements of the correlation matrix that connect to a canonical variable corresponding only to a diagnosis label of a subject among the plurality of attribute information items by successively selecting, from M (M: natural number not smaller than 2) different subsets extracted from the plurality of subjects, one subset and by performing a sparse canonical correlation analysis on the attribute information items and on elements of the correlation matrix of (M-1) subsets except for the selected one subset,
iii) obtain, for the successively selected subsets, a first sum-set as a sum-set of elements of the extracted correlation matrix, and
iv) generate a discriminator for estimating the diagnosis label of a subject from the elements of the first sum-set.

14. The biomarker apparatus according to claim 13, wherein
the one or more first processors are configured to calculates the discriminator for estimating the diagnosis label of a subject from the first sum-set by sparse logistic regression.

15. The biomarker apparatus according to claim 13, wherein
the one or more first processors are further configured to when subjects other than the above-described M subsets of the plurality of subjects are used as a test set and the test set is divided into N (N: natural number not smaller than 2) different groups, perform feature extraction to calculate, by sparse logistic regression, a test discriminator for estimating the diagnosis label of a subject based on the first sum-set, on a set of subjects except for one group selected from the N groups of the plurality of subjects, and for extracting elements of the correlation matrix that become the explanatory variables of the test discriminator in the process of sparsing, and iterate the feature extraction while successively selecting one group from the N groups for obtaining a second sum-set as the sum-set of elements of the correlation matrix extracted as the explanatory variables of test discriminator; and calculate the discriminator for estimating the diagnosis label of a subject from the second sum-set by sparse logistic regression.

16. A biomarker apparatus, comprising:

a storage device storing information for specifying a discriminator generated by one or more first processors from signals obtained by a brain activity detecting device time-sequentially measuring in advance signals representing brain activities at a plurality of prescribed regions in a brain of each of a plurality of subjects; and one or more second processors configured to perform a process of discriminating input data based on the discriminator specified by the information stored in the storage device; wherein a plurality of attribute information items are associated with each of the plurality of subjects;

the discriminator estimates a diagnosis label of a subject based on the input data; and the one or more first processors are programmed to i) calculate, for each of the subjects, a correlation matrix of brain activities among the plurality of prescribed regions from the measured signals, ii) extract elements of the correlation matrix that connect to a canonical variable corresponding only to a diagnosis label of a subject among the plurality of attribute information items by successively selecting, from M (M: natural number not smaller than 2) different subsets extracted from the plurality of subjects, one subset and by performing a sparse canonical correlation analysis on the attribute information items and on elements of the correlation matrix of (M-1) subsets except for the selected one subset, iii) obtain, for the successively selected subsets, a first sum-set as a sum-set of elements of the extracted correlation matrix, and iv) generate a discriminator for estimating the diagnosis label of a subject from the elements of the first sum-set.

17. A non-transitory computer readable medium having stored thereon instructions that cause a computer to execute each of the functions of the biomarker apparatus according to claim 13.

* * * * *